US012741128B2

(12) United States Patent
Tadros et al.

(10) Patent No.: US 12,741,128 B2
(45) Date of Patent: Sep. 22, 2026

(54) MICRONEEDLE PARTICLES, COMPOSITIONS, AND METHODS OF TREATMENT AND DELIVERING A SUBSTANCE OF INTEREST

(71) Applicant: Georgia Tech Research Corporation, Atlanta, GA (US)

(72) Inventors: Andrew Tadros, Atlanta, GA (US); Mark Prausnitz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 229 days.

(21) Appl. No.: 18/775,855

(22) Filed: Jul. 17, 2024

(65) Prior Publication Data

US 2024/0382731 A1 Nov. 21, 2024

Related U.S. Application Data

(60) Division of application No. 17/712,755, filed on Apr. 4, 2022, now Pat. No. 12,070,567, which is a continuation of application No. 16/079,579, filed as application No. PCT/US2017/020160 on Mar. 1, 2017, now Pat. No. 11,291,816.

(60) Provisional application No. 62/301,780, filed on Mar. 1, 2016.

(51) Int. Cl.

| | |
|---|---|
| ***A61K 8/02*** | (2006.01) |
| ***A61K 9/00*** | (2006.01) |
| ***A61K 31/352*** | (2006.01) |
| ***A61M 37/00*** | (2006.01) |
| ***A61Q 19/00*** | (2006.01) |

(52) U.S. Cl.

CPC ....... *A61M 37/0015* (2013.01); *A61K 8/0204* (2013.01); *A61K 8/0245* (2013.01); *A61K 9/0021* (2013.01); *A61K 31/352* (2013.01); *A61Q 19/00* (2013.01); *A61K 2800/87* (2013.01); *A61K 2800/91* (2013.01); *A61M 2037/0023* (2013.01); *A61M 2037/0046* (2013.01); *A61M 2037/0053* (2013.01); *A61M 2037/0061* (2013.01)

(58) Field of Classification Search

None

See application file for complete search history.

(56) References Cited

U.S. PATENT DOCUMENTS

| | | | |
|---|---|---|---|
| 5,536,448 | A | 7/1996 | Takahashi et al. |
| 7,588,825 | B2 | 9/2009 | Bell et al. |
| 2004/0131688 | A1 | 7/2004 | Dov et al. |
| 2005/0209565 | A1 | 9/2005 | Yuzhakov et al. |
| 2007/0161964 | A1 | 7/2007 | Yuzhakov |
| 2008/0213461 | A1 | 9/2008 | Gill et al. |
| 2009/0035446 | A1 | 2/2009 | Kwon |
| 2009/0155591 | A1 | 6/2009 | Jin et al. |
| 2009/0182306 | A1 | 7/2009 | Lee et al. |
| 2010/0031219 | A1 | 2/2010 | Okamoto |
| 2010/0256569 | A1 | 10/2010 | Cachemaille et al. |
| 2010/0312191 | A1 | 12/2010 | Allen et al. |
| 2011/0150787 | A1 | 6/2011 | Gonzales et al. |
| 2011/0223215 | A1 | 9/2011 | Mason |
| 2011/0288485 | A1 | 11/2011 | Tokumoto et al. |
| 2013/0144261 | A1 | 6/2013 | Chowdhury |
| 2013/0331792 | A1 | 12/2013 | Karp et al. |
| 2015/0352345 | A1 | 12/2015 | Sul et al. |
| 2016/0220483 | A1 | 8/2016 | Mistilis et al. |
| 2020/0121900 | A1 | 4/2020 | Kang et al. |

FOREIGN PATENT DOCUMENTS

| | | | |
|---|---|---|---|
| EP | 2946805 | A1 | 11/2015 |
| GB | 2503651 | A | 1/2014 |
| JP | 7350113 | B2 | 9/2023 |
| WO | 2006016364 | A2 | 2/2006 |
| WO | 2013037121 | A1 | 3/2013 |
| WO | 2015164840 | A1 | 10/2015 |

OTHER PUBLICATIONS

Examination report No. 1 issued in Australian application No. 2022202288, dated Jun. 21, 2023 (5 pages).
Notice of Reasons for Rejection issued in Japan application No. 2022-025588, mailed Mar. 20, 2023 (7 pages).
Requisition by the Examiner issued in Canada application No. 3,055,022, dated Jan. 25, 2023 (5 pages).
International Search Report and Written Opinion for PCT/US2017/020160, mailed May 25, 2017 (13 pages).
Raphael et al., Elongate microparticles for enhanced drug delivery to ex vivo and in vivo pig skin, Journal of Controlled Release 2013, 172, pp. 96-104.
Raphael et al., High Aspect Ratio Elongated Microparticles for Enhanced Topical Drug Delivery in Human Volunteers, Adv. Healthcare Mater. 2014, 3, pp. 860-866.
Raphael et al., Recent Advanced in Physical Delivery Enhancement of Topical Drugs, Current Pharmaceutical Design 2015, 21, pp. 2830-2847.
European Search Report for European Patent Application No. 177607704.1 dated Oct. 11, 2019.

(Continued)

*Primary Examiner* — David J Blanchard
*Assistant Examiner* — Daniel F Coughlin
(74) *Attorney, Agent, or Firm* — Eversheds Sutherland (US) LLP

(57) ABSTRACT

Provided herein are microneedle particles, compositions that include microneedle particles, methods of treating skin, and methods of delivering a substance of interest. The microneedle particles may include one or more microneedles, and the microneedle particles may be configured to prevent the entire microneedle particle from penetrating the biological tissue. The microneedle particles may be dispersed in a liquid medium to form a composition. A biological tissue may be contacted with the microneedle particles to pre-treat the biological tissue, and a substance of interest may be applied to the pre-treated biological tissue.

20 Claims, 15 Drawing Sheets

(56) References Cited

OTHER PUBLICATIONS

Japan Office Action, JP Patent Application No. 2018-545168 mailed on Jan. 5, 2021.
1Notice of Reasons for Refusal issued in Japanese application No. 2023-147458, dated Aug. 26, 2024 (6 pages).

500
530
510
520

MICRONEEDLE PARTICLES, COMPOSITIONS, AND METHODS OF TREATMENT AND DELIVERING A SUBSTANCE OF INTEREST

CROSS-REFERENCE TO RELATED APPLICATIONS

This application is a divisional of U.S. patent application Ser. No. 17/712,755, filed Apr. 4, 2022, which is a continuation of U.S. patent application Ser. No. 16/079,579, filed Aug. 24, 2018, now U.S. Pat. No. 11,291,816, which is a U.S. national phase application of international application no. PCT/US17/20160, filed Mar. 1, 2017, which claims priority to U.S. Provisional Patent Application No. 62/301, 780, filed Mar. 1, 2016. The content of these applications is incorporated by reference herein.

BACKGROUND

The delivery of bioactive compounds can be difficult due to the strong barrier functionality of many biological tissues, such as skin, gastrointestinal tract, blood vessels, cellular membranes, etc.

Techniques have been devised to remove portions of a biological tissue, such as the skin's stratum corneum, or otherwise make holes in the barrier layers of tissues. These techniques have included abrasive methods, such as a solid surface coated with abrasive particles (e.g., sandpaper), or liquid/gelatinous preparations containing abrasive particles (e.g., electrocardiogram electrode preparation gel, skin exfoliation formulations). These techniques, however, typically do not create in the biological tissue discrete punctures and, instead, usually create scrapes or scratches that can be long and/or thin. The long and/or thin scrapes or scratches usually [1] do not effectively aid the delivery of bioactive compounds and/or the treatment of the tissue, or [2] cause undesirable tissue damage when the number of scrapes or scratches is sufficient to aid the delivery of bioactive compounds and/or the treatment of the tissue. The tissue damage may be due to the fact that abrading removes tissue in a manner parallel to the tissue surface, thereby removing large areas of tissue in the process of penetrating sufficiently deeply into the tissue.

Other techniques that have been attempted include using needle structures, such as microneedles that are sold for cosmetic uses (e.g., Demaroller), to puncture a biological tissue as a skin pretreatment prior to applying a vaccine (e.g., Bacillus Calmette-Guerin vaccine). These techniques, however, include the use of multiple needle structures that are assembled onto a substrate from which the needles protrude in a substantially perpendicular fashion. The substrates are usually macroscopic in size (e.g., >>1 mm), and/or are usually planar (i.e., two-dimensional) or cylindrical (i.e., two-dimensional in cylindrical coordinates). As a result, the surface area and/or location of the tissue that can be treated with these methods is limited. These methods may also require expertise to administer.

Further techniques for preparing biological tissues include chemical enhancers, electric fields, ultrasound, and other non-invasive methods that make tissues, such as skin, more permeable by introducing nanometer-scale changes in tissue and structure. Ballistic methods also have been used, which typically include shooting particles or other objects at a biological tissue, which puncture the biological tissue. These particles or objects, however, are not generally removed from the tissue immediately after puncture, and are generally completely embedded in (or across) the biological tissue.

Microneedle patches also have been used, but generally are limited by the relatively small surface area that can be covered by the patches, which is typically <10 $cm^2$. This limitation can hinder the use of microneedle patches in numerous medical indications. The use of microneedle patches is further limited by the fact that it is not feasible to use microneedle patches as an additive in a topical formulation, due at least to the fact that ensuring that the microneedles contact the skin instead of the substrate side is difficult, if not impossible. Also, biological tissues that are difficult to access can present difficulties when a microneedle patch is used.

There remains a need to improve devices, compositions, and methods for better control of treatment surface area, treatment location, and/or tissue penetration.

BRIEF SUMMARY

Improved devices, compositions, and methods of treatment and delivering a substance of interest have been developed which address one or more of the above-described needs.

In one aspect, microneedle particles that at least partially penetrate a biological tissue are provided. In embodiments, the microneedle particles comprise a core structure, and one or more microneedles extending from the core structure, the one or more microneedles being structured to penetrate a biological tissue, wherein at least one of (i) the core structure, (ii) the one or more microneedles, and (iii) a spatial relationship between/among two or more of the microneedles is configured to prevent the entire microneedle particle from penetrating the biological tissuc.

In another aspect, compositions comprising microneedle particles are provided. In embodiments, the compositions comprise a plurality of the microneedle particles provided herein, and a liquid medium in which the plurality of microneedle particles is dispersed. The compositions may be adapted for application to a biological tissue surface, such as mammalian skin. The liquid medium, the microneedle particles, or a combination thereof may include a bioactive agent and/or other substance of interest.

In another aspect, methods of delivering a substance of interest are provided. In embodiments, the methods comprise contacting a biological tissue surface with a plurality of the microneedle particles provided herein in a manner effective to form a plurality of microchannels in the biological tissue surface, yielding a pre-treated biological tissue arca, and applying a substance of interest to the pre-treated biological tissue arca.

In still another aspect, methods of treating skin are provided. In embodiments, the methods comprise contacting a region of skin with a plurality of microneedle particles, wherein the plurality of microneedle particles comprises microneedle particles having a core structure and one or more microneedles extending from the core structure, the one or more microneedles having a structure capable of at least partially penetrating skin. In one embodiment, the plurality of microneedle particles is dispersed in a liquid medium.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1A:
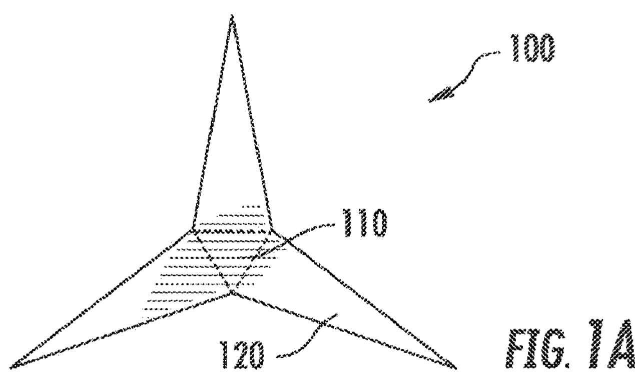
FIG. 1A depicts one embodiment of a microneedle particle having three planar microneedles.

Improved devices and methods of addressing one or more of the difficulties associated with the barrier functionality of biological tissues have been developed. In embodiments, the devices include microneedle particles that are capable of at least partially penetrating a biological tissue, and may [1] offer flexible geometries and/or materials of composition, [2] have the ability to target biological tissues having large surface areas, [3] have the ability to target biological tissues not easily accessible through conventional technologies, [4] have the ability to puncture tissue in a manner that may [i] minimize or eliminate the removal of tissue, [ii] create a pathway that is at least substantially perpendicular to the tissue surface, thereby maximizing penetration to a sufficient depth, or [iii] a combination thereof, or [5] a combination thereof. The microneedle particles provided herein may be applied to a relatively large area of a biological tissue and/or facilitate the delivery of exogenous molecules, including bioactive agents and/or other substances of interest. The microneedle particles provided herein also may be configured to prevent the entire microneedle particle from penetrating the biological tissue.

For example, in a particularly advantageous embodiment, the microneedle particles are configured to be applied onto a selected area of skin; rubbed into and/or wiped across that area of skin to form microchannels therein; and then washed or wiped off the skin. A bioactive agent and/or other substance of interest may be applied to the selected area, for instance with the microneedle particles, for passage into the microchannels. In one case, these steps are carried out with the bioactive agent and/or other substance of interest and the microneedle particles provided in viscous liquid or gel. As a further example, the microneedle particles may comprise a bioactive agent and/or other substance of interest that is delivered via the microchannels.

Microneedle Particles

The microneedle particles are structured to at least partially penetrate a biological tissue, such as the stratum corneum of human skin. That is, the microneedle portions (or at least the tip end portion thereof) of the particles are dimensioned and possess the mechanical rigidity to enable them to be pressed into and penetrate the biological tissue, forming a microscale hole or channel therein, and the microneedle particles each have an overall geometric shape or other design feature that generally prevents the particle as a whole from penetrating into the biological tissue. Mere elastic deformation of the biological tissue is not penetration; penetration may include elastic deformation, but further includes penetration into the tissue.

In some embodiments, this advantageously may facilitate removal of the microneedle particles from the surface of the biological tissue after the desired microchannels are formed therein. For example, after at least partially penetrating a biological tissue, the microneedle particles may be washed or wiped away from the biological tissue, where the microneedle particles are configured to not become completely and/or irremovably embedded in the biological tissue.

In some other embodiments, however, the microneedle particles are configured to prevent the entire structure of the microneedle particles from penetrating a biological tissue, and the microneedle particles have one or more structural features that prevent their removal from the biological tissue and/or that increases the difficulty of removing the microneedle particles from the biological tissue.

In embodiments, the microneedle particles include a core structure and one or more microneedles extending from the core structure. The one or more microneedles may be structured to at least partially penetrate a biological tissue. For example, the one or more microneedles may be structured to at least partially penetrate a biological tissue to form a microchannel in the biological tissue. The one or more microneedles may extend independently in any direction from the core structure. In one embodiment, the one or more microneedles are structured to [1] at least partially penetrate a first type of biological tissue, and [2] prevent or decrease the likelihood that the one or more microneedles can penetrate a second type of biological tissue. The second type of biological tissue, for example, may include the skin of the fingers, while the first type of biological tissue may include a tissue to be treated, for example, an area of the skin having a relatively thinner stratum corneum or a mucosal tissue. In this way, for example, the one or more microneedles may not penetrate, or may be less likely to penetrate, the skin of the fingers used to apply or rub the microneedle particles onto/into the treatment area of the first biological tissue.

In some embodiments, the microneedle particles comprise one microneedle, two microneedles, three microneedles, four microneedles, five microneedles, six microneedles, seven microneedles, eight microneedles, nine microneedles, or ten microneedles extending from the core structure. In a preferred embodiment, the microneedle particles each have from 3 to 10 microneedles. In a particular embodiment, the microneedle particles comprise an odd number of microneedles; for example, one microneedle, three microneedles, five microneedles, seven microneedles, or nine microneedles. In a still further embodiment, the microneedle particles comprise an even number of microneedles; for example, two microneedles, four microneedles, six microneedles, eight microneedles, or ten microneedles. In another embodiment, the microneedle particles comprise 3 to 100 microneedles, 3 to 75 microneedles, 3 to 50 microneedles, 3 to 25 microneedles, 3 to 20 microneedles, or 10 to 20 microneedles.

The core structure typically is the portion of the microneedle particle that connects the microneedles, especially when there are three or more microneedles. When a microneedle particle has only two microneedles, the core structure consists of the portion of the microneedle particle that connects the two microneedles, or the interface between the two microneedles. When a microneedle particle has only one microneedle, the core structure can include the non-penetrating portion of the microneedle particle. Such a non-penetrating portion is provided at the base of the microneedle (distal to the tip) and would include a laterally extending portion (lateral with respect to the longitudinal axis of the microneedle) that is effective to function as a penetration stop. It may be shaped as a ball or a flange, for example.

The core structure may be a solid structure, or a hollow structure having one or more internal cavities. When the core structure has a hollow structure, the core structure may be filled with a material, which may be delivered to a biological tissue. The material, which may be a solid or liquid, may be or include a bioactive agent and/or other substance of interest. The core structure may be configured to expand/swell, which may permit the microneedle particles to be delivered and applied to an internal biological tissue, such as the gastrointestinal tract. Prior to the initiation of expansion/swelling, the one or more microneedles may not penetrate, or may be less likely to penetrate, a biological tissue. The core structure may be configured to expand/swell upon or after reaching a desired location, so that the one or more microneedles only penetrate, or are more likely to penetrate, a biological tissue at or near the desired location.

Various design features of the microneedle particles may be selected to impart the particles with the functionality preventing the entire microneedle particle from penetrating a biological tissue. These features may include the core structure itself, the one or more microneedles themselves, or the spatial relationship between/among the microneedles or a subset of those microneedles. Of course, a combination of these features may be designed to prevent the entire microneedle particle from penetrating a biological tissuc.

For example, the core structure may have a size, shape, and/or a lack of sharp edges that permits one or more microneedles extending from the core structure to penetrate a biological tissue, but that inhibits all or substantially all of the core structure from penetrating into the biological tissue. As a further example, the one or more microneedles may have a structural feature, such as tapering, that permits only a portion of the one or more microneedles to penetrate a biological tissue. For example, a microneedle may have a shoulder or plateau that permits only the portion of the microneedle below the shoulder or plateau to penetrate the biological tissue. Such a configuration may prevent the core structure from contacting the biological tissue. As yet another example, two or more microneedles may be spatially arranged with respect to one another so that as one of the microneedles penetrates a biological tissue, the other microneedle(s) is/are fixed in an orientation that impart(s) resistance to further penetration by the particle, preventing the entire microneedle particle from penetrating the biological tissuc. For example, one microneedle may be oriented toward and into the biological tissue, while one or more other microneedles of the particle extend in a lateral orientation, so that the flat sidewall of at least one of the other microneedles faces the biological tissue. The resistance may be provided when any part of the other microneedle(s) contact(s) the biological tissue. Due at least in part to the fact that the microneedle particle may be configured to prevent the entire microneedle particle from penetrating a tissue surface, a substance of interest delivered by the microneedle particle may be associated with the microneedle particle in a manner and/or at a position that ensures or increases the likelihood that at least a portion of the substance of interest [1] will enter a tissue surface and/or be released beneath a tissue surface, [2] will not enter a tissue surface and/or be released on or above the tissue surface, or [3] a combination thereof.

The one or more microneedles may extend from the core structure in a manner that imparts a symmetrical structure to the microneedle particle. Alternatively, the one or more microneedles may extend from the core structure in a manner that imparts an asymmetrical structure to the microneedle particle. A particle may have an even number of microneedles or an odd number of microneedles.

Generally, the one or more microneedles of a microneedle particle can have the same or different dimensions. In one embodiment, the one or more microneedles of the microneedle particles have substantially the same dimensions. In another embodiment, the one or more microneedles of the microneedle particles have different dimensions. For example, a microneedle particle may have four microneedles, and [1] all four microneedles may have the same dimensions, [2] all four microneedles may have different dimensions, [3] a first pair of the four microneedles may have the same dimensions, and those dimensions may differ from those of the second pair of the four microneedles, and the second pair of the four microneedles can include two microneedles having the same or different dimensions, [4] three of the four microneedles may have the same dimensions, and those dimensions may differ from the dimensions of the fourth microneedle.

The one or more microneedles may have any shape capable of at least partially penetrating a biological tissue. In embodiments, the one or more microneedles are high-aspect-ratio structures having a length at least two times greater than a width. The length of a microneedle is the distance from the core structure to the tip of the microneedle. In one embodiment, each of the one or more microneedles independently has a length of about 1 μm to about 2,000 μm. In one particular embodiment, each of the one or more microneedles independently has a length of about 10 μm to about 2,000 μm. In some embodiments, each of the one or more microneedles independently has a length of about 50 μm to about 2,000 μm. In another embodiment, each of the one or more microneedles independently has a length of about 100 μm to about 1,000 μm. In a further embodiment, each of the one or more microneedles independently has a length of about 250 μm to about 750 μm. In yet another embodiment, each of the one or more microneedles independently has a length of about 100 μm to about 500 μm. In a still further embodiment, each of the one or more microneedles has a length of about 500 μm. In particular embodiments, the microneedle particles comprise one microneedle, two microneedles, three microneedles, four microneedles, five microneedles, six microneedles, seven microneedles, eight microneedles, nine microneedles, or ten microneedles, and each of the microneedles independently has a length of about 1 μm to about 2,000 μm, about 10 μm to about 2,000 μm, about 50 μm to about 2,000 μm, about 100 μm to about 1,000 μm, or about 250 μm to about 750 μm.

In embodiments, at least one dimension of the one or more microneedles may be tapered. For example, one or more dimensions of the one or more microneedles, such as the width and/or height of the one or more microneedles may be greatest at a particular position, such as a position adjacent to the core structure.

The one or more microneedles may have a tip having a width of about 0.1 μm to about 30 μm. In embodiments, the one or more microneedles have a tip having a width of about 0.1 μm to about 30 μm, about 0.1 μm to about 25 μm, about 0.1 μm to about 20 μm, about 0.1 μm to about 15 μm, about 0.1 μm to about 10 μm, about 0.1 μm to about 5 μm, about 1 μm to about 10 μm, about 1 μm to about 7 μm, about 1 μm to about 5 μm, about 1 μm to about 4 μm, or about 1 μm to about 3 μm. In one embodiment, each microneedle has a tip having a width of about 0.1 μm to about 5 μm. The "tip" typically is the portion of the one or more microneedles that first penetrates a biological tissue.

The microneedle particles generally may be of any size, including a size that prevents or reduces the likelihood of the microneedle particle becoming completely or irremovably embedded in the biological tissue. In one embodiment, the greatest dimension of the microneedle particles is about 10 μm to about 10,000 μm, 10 μm to about 5,000 μm, 100 μm to about 10,000 μm, about 250 μm to about 5,000 μm, about 500 to about 2,000 μm, or about 1,000 μm. The "greatest dimension of the microneedle particles" refers to the greatest of the following distances: [1] the distance between the tips of the two microneedles that are the farthest apart (if the microneedle particle includes two or more microneedles), or [2] the farther possible distance between a tip of a microneedle and the side of the core structure that is opposite the side from which the measured microneedle extends. A plurality of microneedle particles may include microneedle particles of one or more sizes.

In embodiments, the one or more microneedles are planar microneedles. The phrase "planar microneedles," as used herein, refers to two or more microneedles, each having either [1] a central axis that extends from the core structure in at least substantially the same plane, or [2] a tip that exists in substantially the same plane. The planar microneedles may include microneedles that extend from the core structure in the same direction, different directions, or a combination thereof. The planar microneedles also may include co-linear planar microneedles, which extend from opposite sides of the core structure in a manner that permits the central axis of each microneedle to at least substantially correspond with a single line.

In one embodiment, the microneedle particles have two planar microneedles, three planar microneedles, four planar microneedles, five planar microneedles, six planar microneedles, seven planar microneedles, eight planar microneedles, nine planar microneedles, or ten planar microneedles.

When the one or more microneedles are planar microneedles, the microneedle particles may have a substantially planar, i.e., flat, structure. The substantially planar, i.e., flat, microneedle particles may have a thickness of about 1 μm to about 1,000 μm, about 5 μm to about 500 μm, about 10 μm to about 250 μm, 50 μm to about 250 μm, about 50 μm to about 200 μm, about 75 μm to about 200 μm, about 75 μm to about 150 μm, about 75 μm to about 125 μm, or about 80 μm to about 120 μm. It was surprisingly discovered that the microneedle particles having a substantially planar, i.e., flat, structure, were effective in the methods provided herein, and that embodiments of the methods provided herein do not require the use of microneedle particles having a non-flat structure. Not wishing to be bound by any particular theory, it was believed that instead of sliding across tissue surfaces without penetrating the tissue surfaces, as expected, the microneedle particles provided herein were able to at least partially penetrate tissue surfaces due at least in part to the elastically deformable nature of the tissue surfaces, which can create "peaks" and "valleys" on the surface that microneedles can puncture when moving across the tissue surface. The tissue surfaces may be deformed, thereby facilitating penetration, by the one or more forces applied to the tissues by the microneedle particles.

Figure 1B:
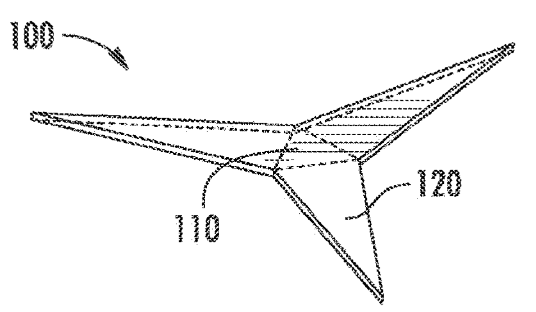
FIG. 1B is a perspective view of the planar microneedle of FIG. 1A.
Figure 2A:
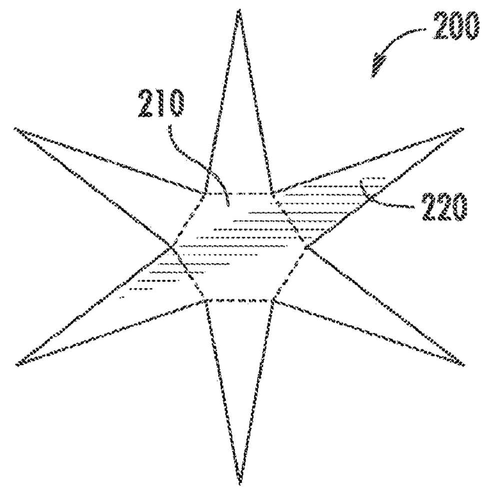
FIG. 2A depicts one embodiment of a microneedle particle having six planar microneedles.
Figure 2A:
Figure 2B:
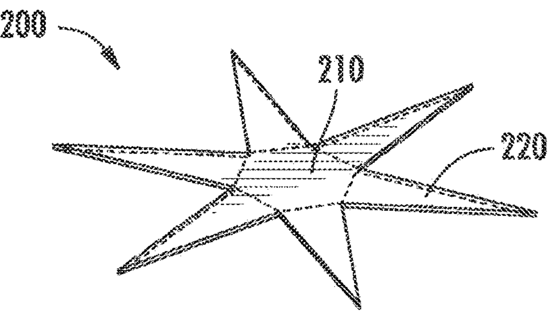
FIG. 2B is a perspective view of the planar microneedle of FIG. 2A.

FIG. 1A and FIG. 1B (perspective view) depict one embodiment of a planar microneedle particle 100 having a core structure 110 from which three planar microneedles 120 extend. FIG. 2A and FIG. 2B (perspective view) depict one embodiment of a planar microneedle 200 having a core structure 210 from which six planar microneedles 220 extend.

In embodiments, the one or more microneedles are planar microneedles, but the microneedle particles have a non-planar, i.e., non-flat, structure. The non-planar structure of the microneedle particles may be imparted by the configuration of the core structure, the configuration of at least one of the planar microneedles, or a combination thereof. For example, the one or more planar microneedles may have a tapered shape that imparts the microneedle particle with a non-flat structure.

Figure 3A:
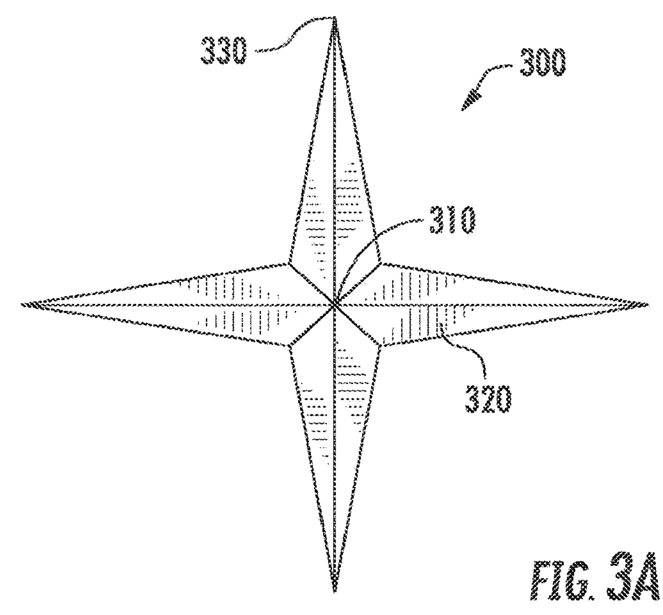
FIG. 3A depicts an embodiment of a microneedle particle having four planar and tapered microneedles.
Figure 3B:
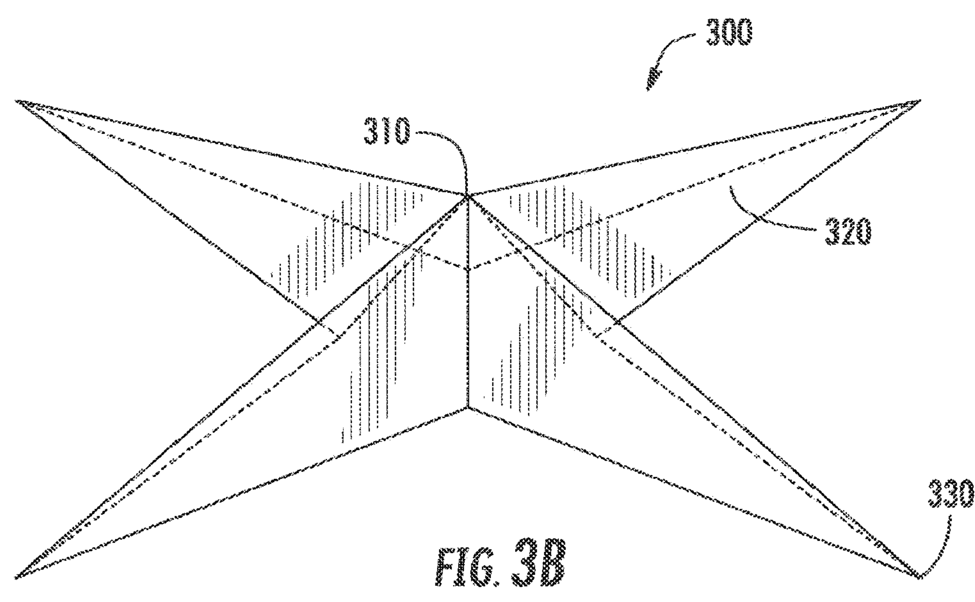
FIG. 3B is a perspective view of the microneedle particle of FIG. 3A.
Figure 3C:
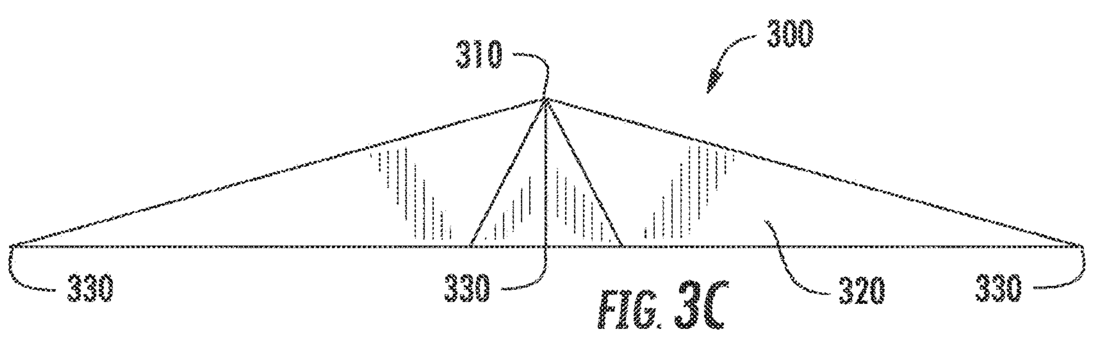
FIG. 3C is a side view of the microneedle particle of FIG. 3A.

FIG. 3A (plan view), FIG. 3B (perspective view), and FIG. 3C (side view) depict an embodiment of a microneedle particle 300 having a core structure 310 from which four planar and tapered microneedles 320 extend. FIG. 3C depicts the tips 330 that exist in substantially the same plane.

Figure 4A:
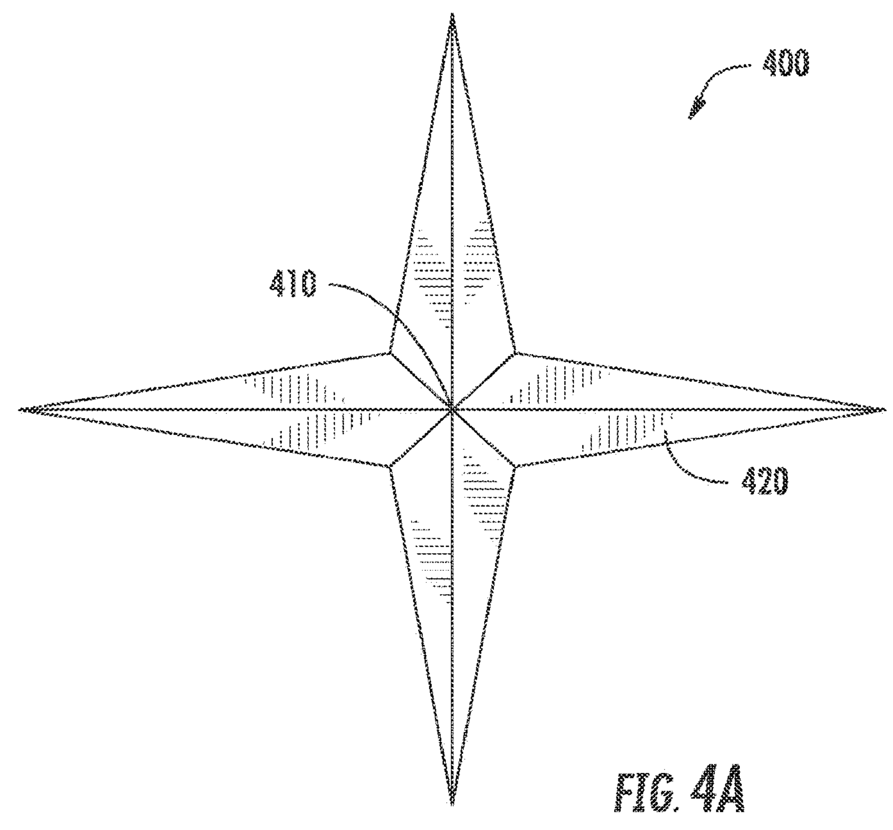
FIG. 4A depicts one embodiment of a microneedle particle having four planar and tapered microneedles.
Figure 4B:
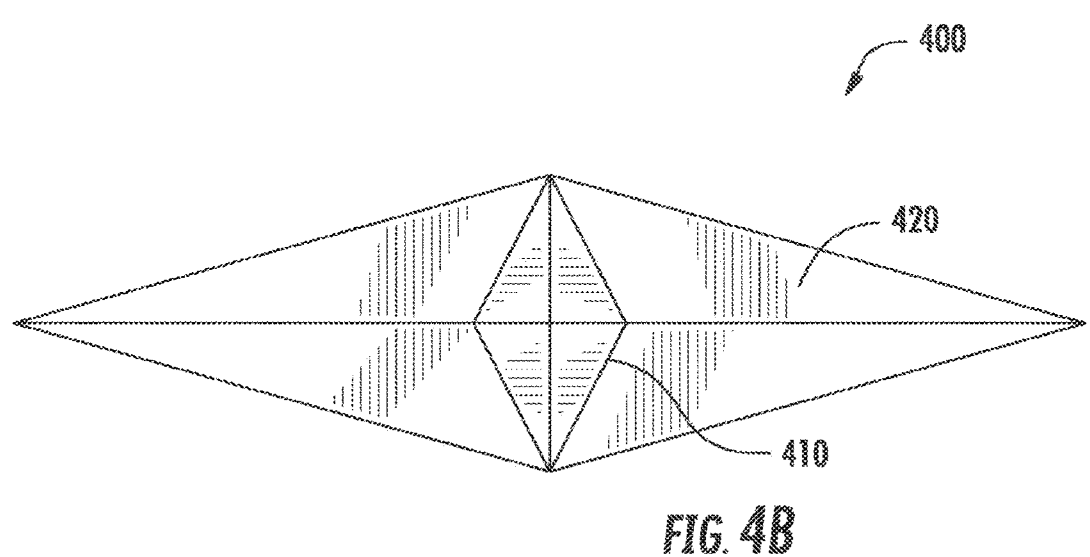
FIG. 4B is a side view of the microneedle particle of FIG. 4A.

FIG. 4A (plan view) and FIG. 4B (side view) depict an embodiment of a microneedle particle 400 having a core structure 410 from which four planar and tapered microneedles 420 extend. Each of the four planar and tapered microneedles 420 has a central axis that extends from the core structure 410 in substantially the same planc.

When viewed in cross-section, the one or more microneedles may have a polygonal shape, a non-polygonal shape, a bisected non-polygonal shape, or a combination thereof. For example, a microneedle particle may include at least one microneedle having a non-polygonal shape when viewed in cross-section, and at least one microneedle having a polygonal shape when viewed in cross-section. As a further example, at least one microneedle of a microneedle particle may include at least one polygonal shape and at least one non-polygonal shape when viewed in cross-section at different positions. Non-limiting examples of non-polygonal shapes include circular, substantially circular, oval, and substantially oval. When a microneedle has a non-polygonal shape when viewed in cross-section, the microneedle may be at least substantially conical in shape, or at least a portion of the structure of the microneedle may be at least substantially conical. The phrase "bisected non-polygonal shape" refers to a polygonal shape that includes a bisecting flat surface. Non-limiting examples of bisected non-polygonal shapes include semi-circular, substantially semi-circular, semi-oval, and substantially semi-oval. Non-limiting examples of polygonal shapes include triangular, square, rectangular, trapezoidal, diamond, pentagonal, hexagonal, septagonal, and octagonal. When a microneedle has a polygonal shape, such as triangular or square, the microneedle may be a pyramidal microneedle.

In embodiments, the one or more microneedles include non-planar microneedles. The phrase "non-planar microneedles," as used herein, refers to microneedles having a central axis that extends from the core structure in different planes. In one embodiment, the one or more microneedles of the microneedle particle are non-planar microneedles. In another embodiment, the one or more microneedles include at least two planar microneedles, and at least one microneedle that is non-planar relative to the pair of planar microneedles. For example, a microneedle particle may have a substantially tetrahedral arrangement of four microneedles provided by two planar microneedles, and, relative to the two planar microneedles, two non-planar microneedles. As a further example, a microneedle particle may have a substantially octahedral arrangement of the one or more microneedles provided by four planar microneedles, and, relative to the four planar microneedles, two non-planar microneedles. As an additional example, a microneedle particle may have a group of planar microneedles, such as three, four, five, or six planar microneedles, and, relative to the group of planar microneedles, one non-planar microneedle.

Figures 5A, 5B, 5C:
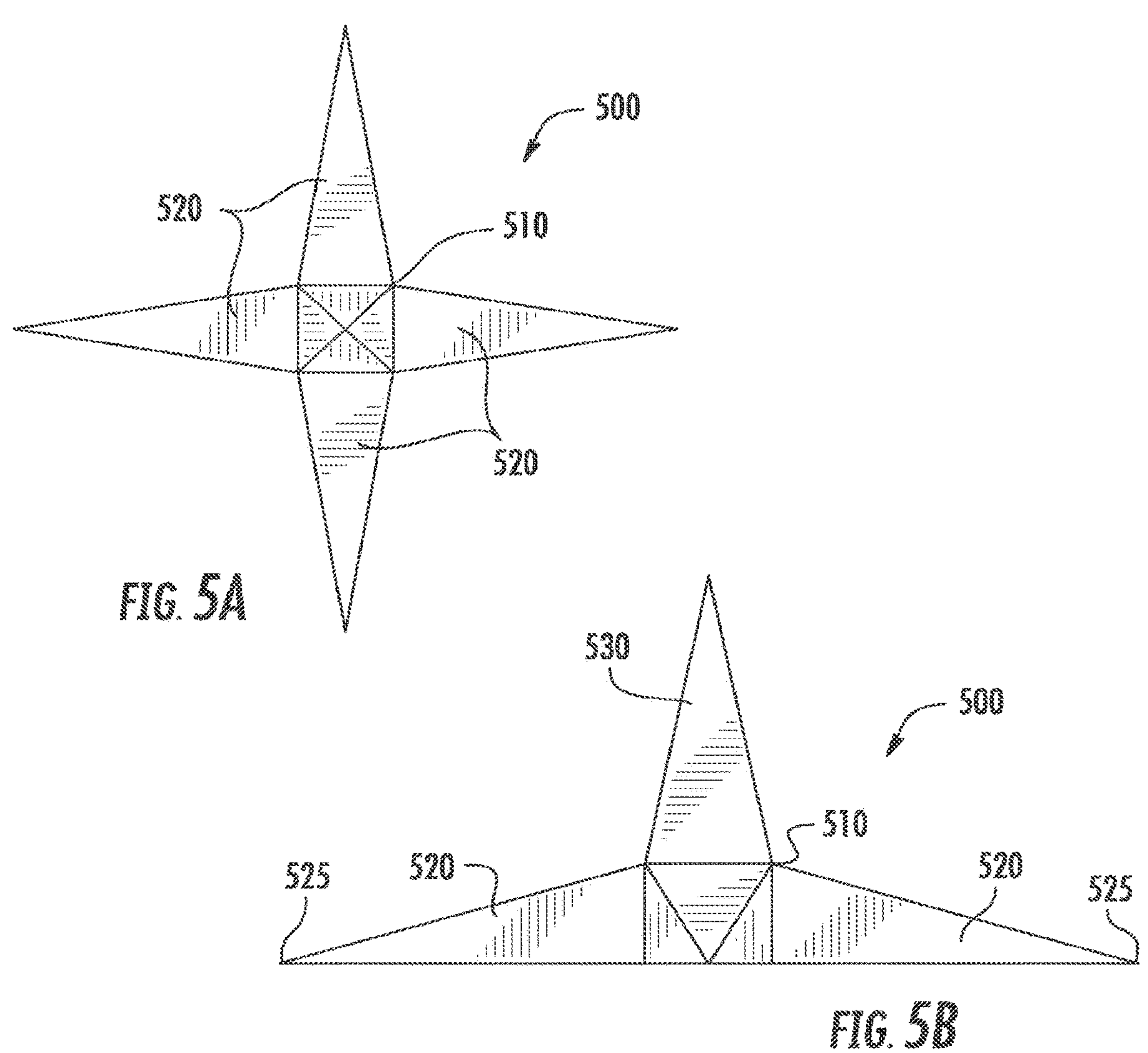
FIG. 5A depicts one embodiment of a microneedle particle have four planar microneedles and one non-planar microneedle.
FIG. 5B is a side view of the microneedle particle depicted at FIG. 5A.
FIG. 5C is a perspective view of the microneedle particle depicted at FIG. 5A.

FIG. 5A (plan view), FIG. 5B (side view), and FIG. 5C (perspective vicw) depict one embodiment of a microneedle particle 500 having a core structure 510 from which four planar microneedles 520 and one non-planar microneedle 530 extend. The microneedles (520, 530) are square-shaped when viewed in cross-section. The four planar microneedles 520 each have a tip 525 that exists in the same planc.

Figure 6A:
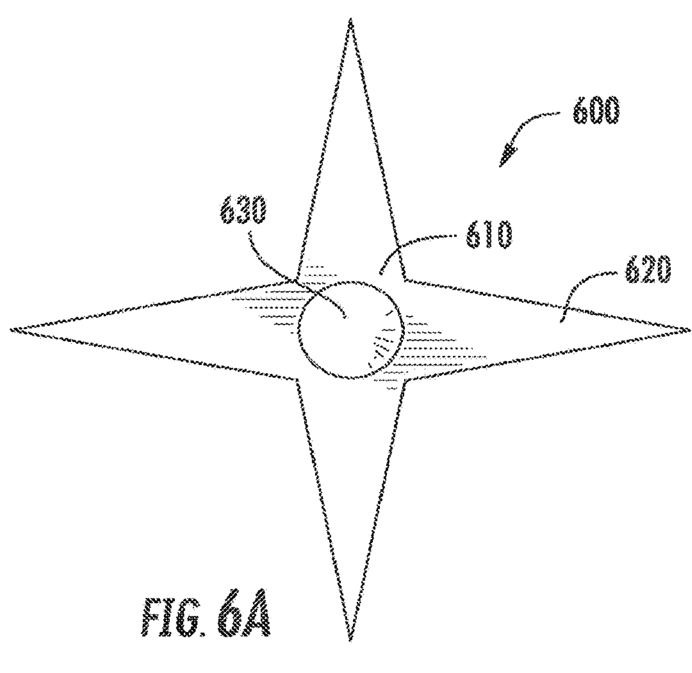
FIG. 6A depicts one embodiment of a microneedle particle having four planar microneedles and one non-planar microneedle.
Figure 6B:
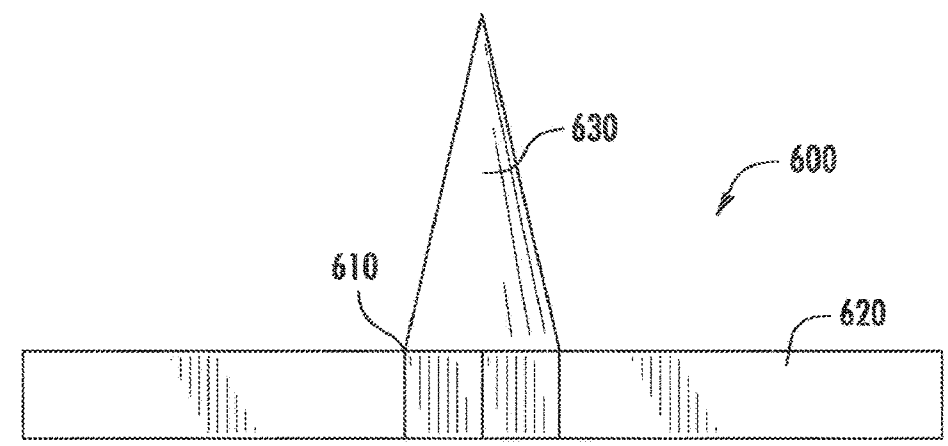
FIG. 6B is a side view of the microneedle depicted at FIG. 6A.
Figure 6C:
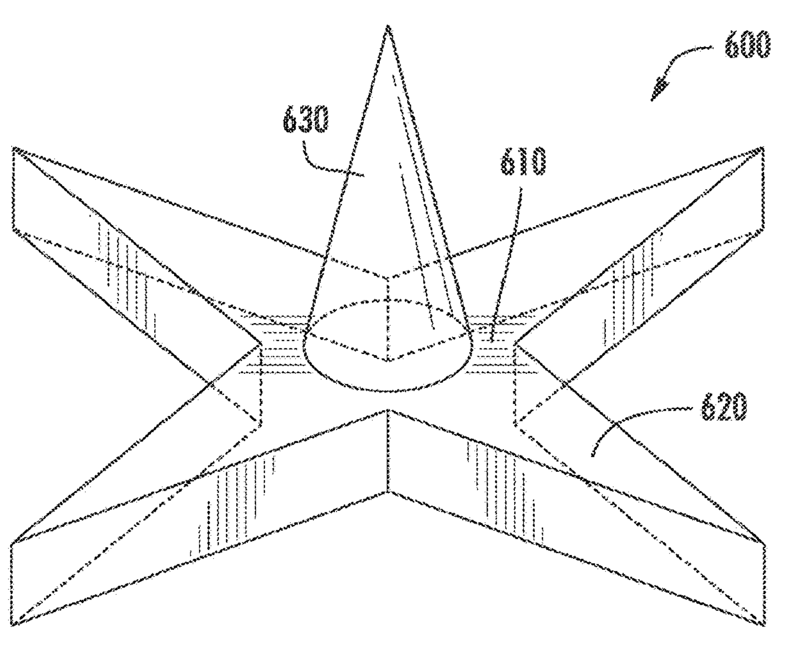
FIG. 6C is a perspective view of the microneedle depicted at FIG. 6A.

FIG. 6A (plan view), FIG. 6B (side view), and FIG. 6C (perspective view) depict one embodiment of a microneedle particle 600 having a core structure 610 from which four planar microneedles 620, and one non-planar microneedle 630 extend. The four planar microneedles 620 are rectangular when viewed in cross-section, and the non-planar microneedle 630 is circular when viewed in cross-section.

Figure 7A:
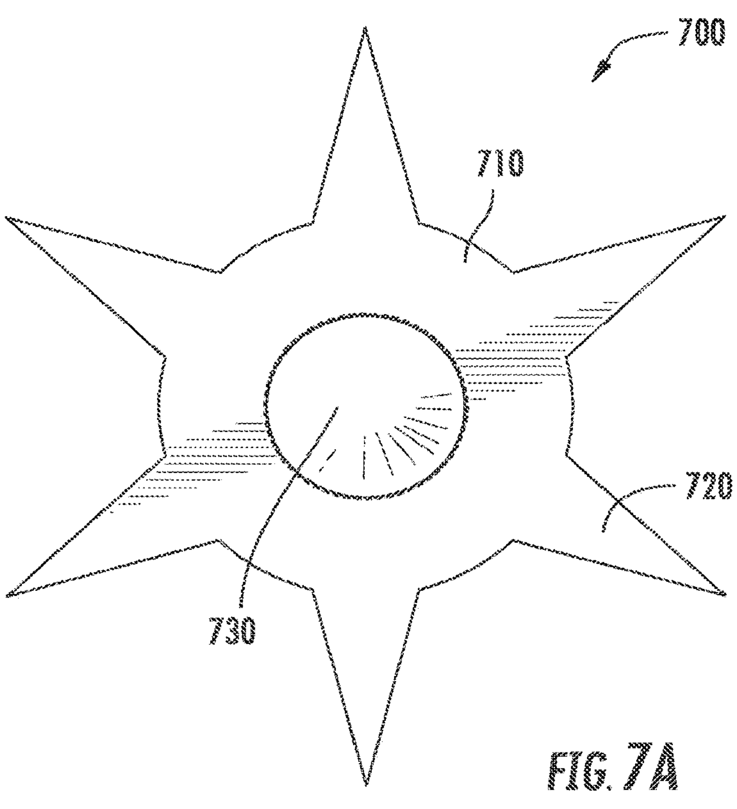
FIG. 7A depicts one embodiment of a microneedle particle having six planar microneedles and two non-planar microneedles.
Figure 7B:
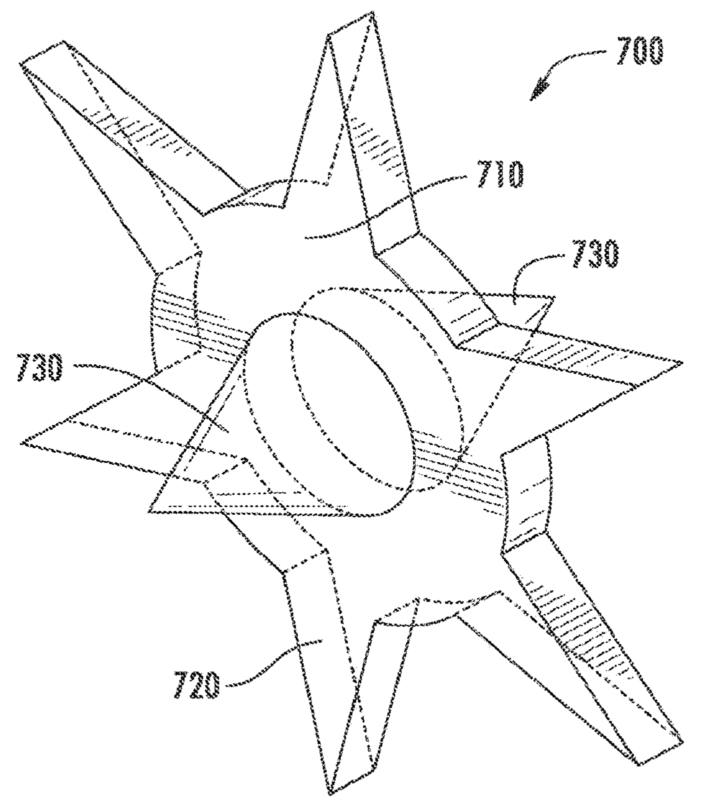
FIG. 7B is a perspective view of the microneedle particle of FIG. 7A.

FIG. 7A (plan view) and FIG. 7B (perspective view) depict one embodiment of a microncedle particle 700 having a core structure 710 from which six planar microneedles 720, and two non-planar microneedles 730 extend. The six planar microneedles 720 are rectangular when viewed in cross-section, and the two non-planar microneedles 730 are circular when viewed in cross-section.

In embodiments, at least one of the one or more microneedles is barbed. In other words, a microneedle of the particle may include one or more barbs. For example, a microneedle particle may include four microneedles, and one, two, three, or four of the microneedles may be barbed microneedles. A barbed microneedle generally is a microneedle having a structural feature rendering it difficult, if not impossible, in the absence of fracturing and/or croding to remove the barbed microneedle from a biological tissue after the barbed microneedle at least partially penetrates the biological tissue. The barbed microneedle may include one or more projections angled away from the tip of the microneedle that at least partially penetrates a biological tissue. For example, a barbed microneedle may have a "fish hook" configuration in which one projection is angled away from the tip of the microneedle, or a barbed microneedle may have an "arrowhead" configuration in which two or more projections are angled away from the tip of the microneedle. The projections may have lincar edges, curved edges, or a combination thereof.

Figure 8:
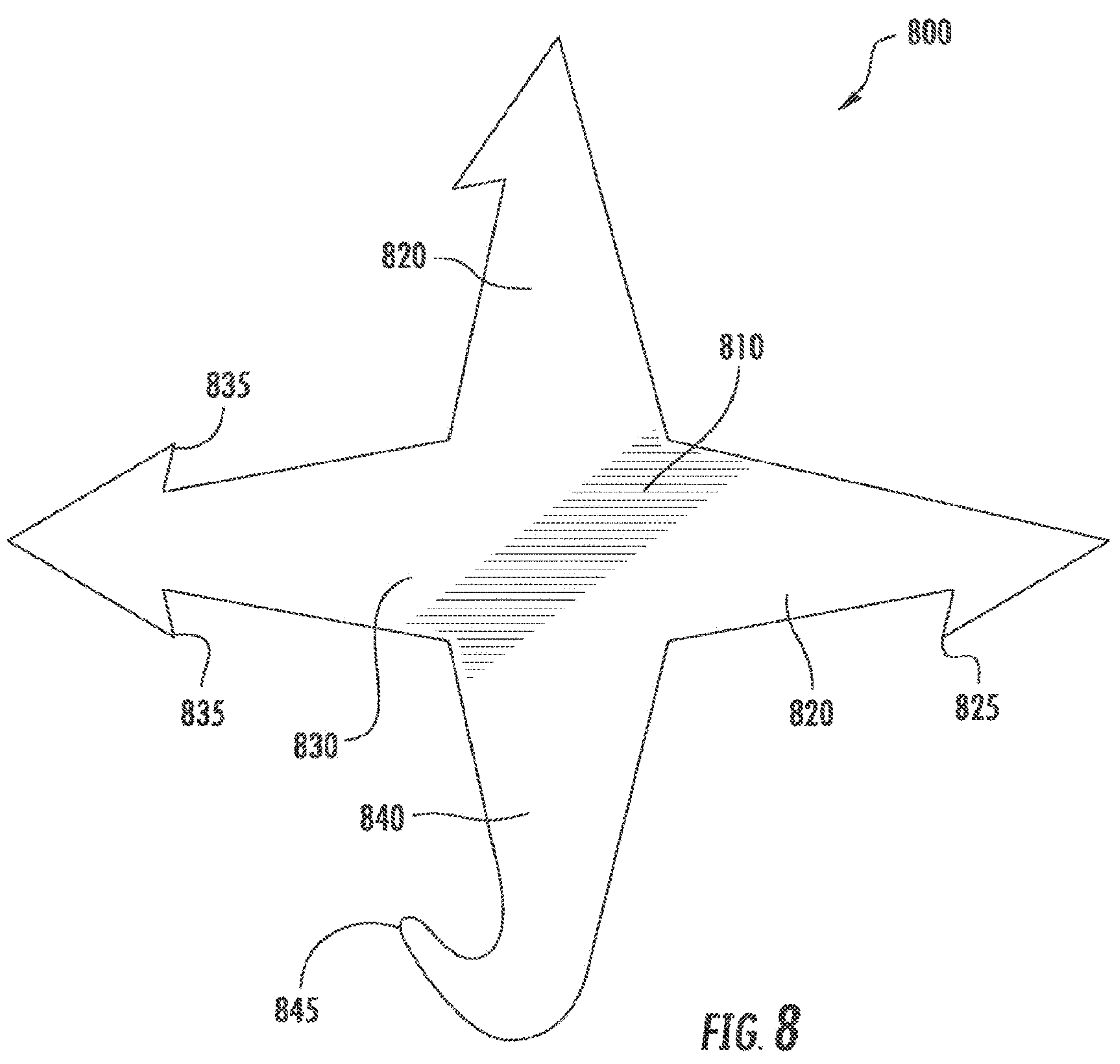
FIG. 8 is a depiction of one embodiment of a microneedle particle having barbed microneedles.

FIG. 8 depicts one embodiment of a microneedle particle 800 having a core structure 810 from which four planar, barbed microneedles (820, 830, 840) extend. Two of the microncedles 820 include one lincar-edged projection 825 angled away from the tip of the microneedles, one of the microneedles 830 has two lincar-edged projections 835 angled away from the tip of the microneedle, and one of the microneedles 840 has one curved-edge projection 845 angled away from the tip of the microneedle.

In embodiments, the barbed microneedles that have at least partially penetrated a biological tissue may be configured to fracture upon removal of the microneedle particle from a biological tissue. Upon fracturing, at least a portion of the barbed microneedle may remain in and/or on the biological tissue. The portion of the barbed microneedle that remains in and/or on the biological tissue may include a substance of interest, such as a bioactive agent, which may include a pharmaceutical agent, a sensor, or a combination thereof. For example, the portion of the barbed microneedle that remains in and/or on the biological tissue may include a slow release formulation that releases a pharmaceutical agent during a desired dosage period. In one embodiment, the fracturing of the barbed microneedle occurs at or near the core structure. In another embodiment, the fracturing of the barbed microneedle occurs at or near the portion of the microneedle that is exposed to the greatest force when the barbed microneedle resists removal from the biological tissue. The barbed microneedles may include a predefined fracture region to ensure or at least increase the likelihood that the fracturing occurs at a desired location. The pre-defined fraction region may include a substantially narrowed portion, a perforated portion, a scored portion, a notched portion, an interface of different materials, or a combination thereof.

Generally, the one or more microneedles of the microneedle particles may include any structural feature that may assist with [1] the at least partial penetration of a biological tissue, [2] the treatment of a biological tissue, [3] reducing the likelihood of or preventing the removal of the one or more microneedles from a biological tissue, [4] the delivery of the microneedle particles to a particular biological tissue, [5] the fracturing of the microneedle particles, [6] the delivery of a substance of interest, or a [7] a combination thereof. For example, each of the one or more microneedles of the microneedle particles independently may be barbed, curved, perforated, hollow, pocketed, swellable/expandable, or a combination thereof.

The one or more microneedles may be configured to reduce or eliminate the microneedles' ability to at least partially penetrate a biological tissue after use. In one embodiment, upon penetrating a biological tissue at least once, at least one of the one or more microneedles are configured to fail mechanically, thereby preventing the at least one of the one or more microneedles from re-penetrating the biological tissue. In another embodiment, upon penetrating a biological tissue at least once, at least one of the one or more microneedles are configured to fail chemically, thereby preventing the at least one of the one or more microneedles from re-penetrating the biological tissue. In yet another embodiment, upon penetrating a biological tissue at least once, at least one of the one or more microneedles are configured to fail mechanically and chemically, thereby preventing the at least one of the one or more microneedles from re-penetrating the biological tissue. The mechanical and/or chemical failures may occur after the one or more microneedles penetrate a biological tissue once, twice, three times, or more. Non-limiting examples of mechanical failures include damaging the microneedles to change their shape and/or dull their tip. Non-limiting examples of chemical failures include at least partially dissolving a portion of the microneedles, thereby dulling and/or causing changes to the microneedle shape and/or mechanical properties.

The microneedle particles may be made of one or more biocompatible materials, such as metals, polymers, ceramics, bioactive agents, sugars, sugar alcohols, or a combination thereof. The bioactive agents generally may include one or more drugs, one or more sensors, one or more cosmeceuticals, or a combination thereof. Therefore, the microneedle particles may be made of a combination of bioactive components (drugs, sensors, cosmeceuticals, or a combination thereof) and inactive components (metals, polymers, ceramics, sugars, etc.). If a portion of the microneedle particle remains in and/or on a biological tissue after removal of the microneedle particle, then the portion of the microneedle particle remaining in and/or on the biological tissue may include at least one bioactive component, at least one inactive component, or a combination thereof.

In one embodiment, the microneedle particle is formed of a substance of interest, such as a bioactive agent. That is, the particle is entirely or substantially constructed of a bioactive substance. "Substantially constructed" as used herein means at least 60% by weight the bioactive substance.

In one embodiment, the microneedle particles are made of water-insoluble material(s). In another embodiment, the microneedle particles are made of, or include, at least one water-soluble and/or biocrodible material. When the microneedle particles are made of water-soluble and/or bioerodible material(s), the microneedle particles or a portion thereof may safely degrade if left in a biological tissue, or after disposal. In one example, the microneedle particle has a matrix structure and a substance of interest, such as a bioactive agent, dispersed in the matrix structure. The matrix structure may consist of or include a water-soluble or bioerodible material. Therefore, one or more microneedles of the microneedle particles may be dissolvable, and if left in the skin will dissolve within the interstitial fluid, and may release a bioactive agent and/or other substance of interest into the skin if configured to do so. As used herein, the term "bioerodible" means that the structure/material degrades in vivo by dissolution, enzymatic hydrolysis, erosion, resorption, or a combination thereof. In a preferred embodiment, the substance of interest and a matrix material in which the substance of interest is dispersed form the structure of the microneedle particle. In a preferred embodiment, the matrix material of the biocrodible microneedle particle is water soluble, such that the entire microneedle particle dissolves in vivo. In another embodiment, the matrix material of the biocrodible microneedle particle is biodegradable, such that the microneedle particles are not soluble in the form originally inserted into the biological tissue, but undergo a chemical change in the body (e.g., break chemical bonds of a polymer) that renders the products of the chemical change (e.g., monomers or oligomers of the polymer) that are water soluble or otherwise can be cleared from the body.

In one embodiment, the microneedle particle is a metal microneedle particle. A metal microneedle particle is one in which the entire structure of the microneedle particle is made of metal. In another embodiment, the microneedle particle is a polymeric microneedle particle. A polymeric microneedle particle is one in which the entire structure of the microneedle particle is made of one or more polymeric materials. In yet another embodiment, the microneedle particle has a structure that is formed of at least one metal and at least one polymeric material. When the microneedle particle includes a polymeric material, the microneedle particle may have a structure comprising a polymeric matrix and a substance of interest dispersed in the polymeric matrix. The substance of interest, such as a bioactive agent, may be at least substantially evenly dispersed or unevenly dispersed in the polymeric matrix. A bioactive agent dispersed in the polymeric matrix may include one or more drugs, one or more sensors, one or more cosmeceuticals, or a combination thereof. The substance of interest may be dispersed in at least a portion of the polymeric matrix that forms or is part of the core structure, at least one of the one or more microneedles, the tip of at least one of the one or more microneedles, the barb of at least one of the one or more microneedles, the non-barbed portion of at least one of the one or more microneedles, or a combination thereof. The non-barbed portion of a microneedle may be the portion of the microneedle that remains attached to the core structure if the barb dissolves or is separated from the microneedle particle. A substance of interest also may be encapsulated, i.e., disposed within porosities and/or voids in the microneedle particle, by any techniques known in the art, such as those of U.S. Pat. Nos. 7,918,814 and 8,257,324, each of which is incorporated herein by reference.

At least a portion of a substance of interest may be released from a microneedle particle [1] before, while, and/or after the microneedle particle has at least partially penetrated a biological tissue, [2] while and/or after the microneedle particle is actively applied to a biological tissue, [3] while the microneedle particle is in contact with a biological tissue, [4] upon and/or after the removal of the microneedle particle from the biological tissue when a portion of the microneedle particle remains on and/or in the biological tissue, or [5] a combination thereof.

At least a portion of a substance of interest may be released from a microneedle particle by one or more mechanisms, including, but not limited to, [1] diffusion through a portion of the microneedle particle, [2] dissolution into a biological tissue, [3] mechanical separation from the microneedle particle (e.g., peeling, breaking, or crumbling off), [4] cleavage of a covalent and/or non-covalent bond (e.g., hydrolytic or enzymatic bond cleavage), [5] cleavage of a physicochemical force (e.g., change in electrostatic interactions due to pH change), [6] swelling/deswelling of a material of which at least a portion of the microneedle particle is formed (e.g., a gel), [7] a phase change of a material of which at least a portion of the microneedle particle is formed (e.g., melting, due, for example, to a temperature change), or [8] a combination thereof.

The microneedle particles provided herein may be made by any suitable method capable of forming a desired geometric shape of the microneedle particles. Non-limiting examples of such methods include molding, mechanical or chemical etching, laser cutting, 3D printing, or other microfabrication techniques known in the art. For example, the microneedle particles may be formed by laser etching a sheet of a material. As a further example, the microneedle particles may be made using a molding process that may include placing a material of construction in a mold having cavities that correspond to the desired geometry of the resulting microneedle particles. The material of construction may be a polymer or precursor thereof, and may be loaded into the mold in a powder or liquid form (e.g., molten polymer and/or polymer dissolved or dispersed in a liquid medium), and then solidified into solid monolithic form in the mold. In another example, an array of discrete particles is formed from a solid sheet of the material by a process that includes at least one of etching, punching, or cutting, such as laser cutting. The microneedle particles also may be sintered. Not wishing to be bound by any particular theory, it is believed that sintering may sharpen the edges and/or tips of the microneedle particles.

In embodiments, the microneedle particle is at least partially coated with a coating composition comprising a bioactive agent and/or other substance of interest. The coating composition, in one embodiment, is applied to the entire surface of the microneedle particle. In another embodiment, the coating composition is applied to at least a portion of the one or more microneedles, the core structure, or a combination thereof. For example, the coating composition may be applied to the core structure, at least one of the one or more microneedles, the tip of at least one of the one or more microneedles, the barb of at least one of the one or more microneedles, or the non-barbed portion of at least one of the one or more microneedles. The coating composition may remain in and/or on the biological tissue upon removal of the microneedle particles. The bioactive agent of the coating composition may include one or more drugs, one or more sensors, one or more cosmeceuticals, or a combination thereof. The coating composition may be applied to the microneedle particles using any technique known in the art, including those of U.S. Patent Application Publication No. 2008/0213461, which is incorporated herein by reference.

As used herein, the term "substance of interest" includes active pharmaceutical ingredients, vaccines, allergens, vitamins, cosmetic agents, cosmeceuticals, diagnostic agents, sensors, markers (e.g., colored dyes or radiological dyes or markers), other bioactive agents, and other materials that are desirable to introduce into and/or on a biological tissue.

In one embodiment, the substance of interest is a prophylactic, therapeutic, or diagnostic agent useful in medical or veterinary application. In one embodiment, the substance of interest is a prophylactic or therapeutic substance, which may be referred to herein as an active pharmaceutical ingredient, i.e., API. In certain embodiments, the API is selected from suitable proteins, peptides and fragments thereof, DNA, RNA, and other natural and unnatural nucleic acid-based molecules and fragments thereof, which can be naturally occurring, synthesized or recombinantly produced. Representative examples of types of API for delivery include antibiotics, antiviral agents, analgesics, anesthetics, antihistamines, antiinflammatory agents, anticoagulants, allergens, antincoplastic agents. In certain embodiments, the API is a dermatological agent used for prophylaxis, therapy, or diagnosis of indications associated with the skin.

In one embodiment, the substance of interest comprises a vaccine. Examples of vaccines include vaccines for infectious diseases, therapeutic vaccines for cancers, neurological disorders, allergies, and smoking cessation or other addictions. Some examples of current and future vaccines for the prevention of anthrax, cervical cancer (human papillomavirus), dengue fever, diphtheria, Ebola, hepatitis A, hepatitis B, hepatitis C, haemophilus influenzae type b (Hib), HIV/AIDS, human papillomavirus (HPV), influenza (seasonal and pandemic), Japanese encephalitis (JE), lyme disease, malaria, measles, meningococcal, monkeypox, mumps, pertussis, pneumococcal, polio, rabies, rotavirus, rubella, shingles (herpes zoster), smallpox, tetanus, typhoid, tuberculosis (TB), varicella (chickenpox), West Nile, and yellow fever.

In another embodiment, the substance of interest comprises a therapeutic agent. The therapeutic agent may be selected from small molecules and larger biotechnology produced or purified molecules (e.g., peptides, proteins, DNA, RNA). Examples of therapeutics, which may include their analogues and antagonists, include but are not limited to insulin, insulin-like growth factor, insultropin, parathyroid hormone, pramlintide acetate, growth hormone release hormone, growth hormone release factor, mecasermin, Factor VIII, Factor IX, antithrombin III, protein C, protein S, β-gluco-cerebrosidase, alglucosidase-a, laronidase, idursulphase, galsulphase, agalsidase-β, a-1 proteinase inhibitor, lactase, pancreatic enzymes, adenosine deaminase, pooled immunoglobulins, human albumin, erythropoictin, darbepoctin-a, filgrastim, pegfilgrastim, sargramostim, oprelvekin, human follicle-stimulating hormone, human chorionic gonadotropin, lutropin-a,interferon (alpha, beta, gamma), aldesleukin, alteplase, reteplase, tenecteplase, urokinase, factor Vila, drotrecogin-a, salmon calcitonin, exenatide, octreotide, dibotermin-a, recombinant human bone morphogenic protein 7, histrelin acetate, palifermin, becaplermin, trypsin, nesiritide, botulinμm toxin (types A and B), collagenase, human deoxyribonuclease I, hyaluronidase, papain, 1-asparaginase, peg-asparaginasc, rasburicase, lepirudin, bivalirudin, streptokinase, anistreplase, bevacizumab, cetuximab, panitumumab, alemtuzumab, rituximab, trastuzumab, abatacept, anakinra, adalimumab, etanercept, infliximab, alefacept, cfalizuman, natalizumab, eculizumab, antithymocyte globulin, basiliximab, daclizumab, muromonab-CD3, omalizumab, palivizumab, enfuvirtide, abciximab, pegvisomant, crotalidene polyvalent fab (ovine), digoxin immune serμm fab (ovine), ranibizumab, denilcukin diftitox, ibritumomab tiuxetan, gemtuzumab ozogamicin, tositumomab, I-tositumomab, antirhesus (rh) immunoglobulin G, desmopressin, vasopressin, deamino [Val4, D-Arg8] arginine vasopressin, somatostatin, somatotropin, bradykinin, bleomycin sulfate, chymopapain, glucagon, epoprostenol, cholecystokinin, oxytocin, corticotropin, prostaglandin, pentigetide, thymosin alpha-1, alpha-1 antitrypsin, fentanyl, lidocaine, epinephrine, sumatriptan, benztropine mesylate, liraglutide, fondaparinux, heparin, hydromorphone, omacetaxine mepesuccinate, pramlintide acetate, thyrotropin-alpha, glycopyrrolate, dihydroergotamine mesylate, Bortezomib, triptoreline pamaote, teduglutide, methylnaltrexone bromide, pasireotide, ondansetron hydrochloride, droperidol, triamcinolone (hex)acetonide, aripiprazole, estradiol valerate, morphine sulfate, olanzapine, methadone hydrochloride, and methotrexate.

In yet another embodiment, the substance of interest is a vitamin, herb, or dietary supplement known in the art. Non-limiting examples include 5-HTP (5-hydroxytryptophan), acai berry, acetyl-L-carnitine, activated charcoal, aloe vera, alpha-lipoic acid, apple cider vinegar, arginine, ashitaba, ashwagandha, astaxanthin, barley, bee pollen, beta-alanine, beta-carotene, beta-glucans, biotin, bitter melon, black cherry, black cohosh, black currant, black tea, branched-ahain amino acids, bromelain (bromelin), calciμm, camphor, chamomile, chasteberry, chitosan, chlorella, chlorophyll, choline, chondroitin, chromiμm, cinnamon, citicoline, coconut water, coenzyme Q10, conjugated linoleic acid, cordyceps, cranberry, creatine, D-mannose, damiana, deer velvet, DHEA, DMSO, echinacea, EDTA, elderberry, emu Oil, evening primrose oil, fenugreek, feverfew, folic acid, forskolin, GABA (gamma-aminobutyric acid), gelatin, ginger, ginkgo biloba, ginseng, glycine, glucosamine, glucosamine sulfate, glutathione, gotu kola, grape seed extract, green coffee, guarana, guggul, gymnema, hawthorn, hibiscus, holy basil, horny goat weed, inulin, iron, krill oil, L-carnitine, L-citrulline, L-trypotophan, lactobacillus, magnesiμm, magnolia, milk thistle, MSM (methylsulfonylmethane), niacin, olive, omega-3 fatty acids, oolong tea, oregano, passionflower, pectin, phenylalanine, phosphatidylserine, potassiμm, probiotics, progesterone, quercetin, ribose, red yeast rice, reishi mushroom, resveratrol, roschip, saffron, SAM-e, saw palmetto, schisandra, sea buckthorn, seleniμm, senna, slippery elm, St. John's wort, stinging nettle, tea tree oil, theanine, tribulus terrestris, turmeric (curcumin), tyrosine, valerian, vitamin A, vitamin B12, vitamin C, vitamin D, vitamin E, vitamin K, whey protein, witch hazel, xanthan gum, xylitol, yohimbe, and zinc.

In yet another embodiment, the substance of interest comprises a therapeutic agent used in dermatology. The therapeutic agent may be selected from small molecules and large biotechnology produced or purified molecules (e.g., peptides, proteins, DNA, RNA). A therapeutic agent used in dermatology may be an agent used to treat any skin condition, or combination of skin conditions, including bacterial infection, viral infection, fungal infection, alopecia, psoriasis, dermatitis, or photo damaged skin. Examples of antifungal drugs include, but are not limited to, amorolfine, naftifine, terbinafine, fluconazole, itraconazole, ketoconazole, posaconazole, ravuconazole, voriconazole, clotrimazole, butoconazole, cconazole, miconazole, oxiconazole, sulconazole, terconazole, tioconazole, caspofungin, micafungin, anidulafingin, amphotericin B, AmB, nystatin, pimaricin, griseofulvin, ciclopirox olamine, haloprogin, tolnaftate, undecylenate, or combinations thereof. Examples of an antiviral drugs include, but are not limited to, acyclovir, penciclovir, famciclovir, valacyclovir, behenyl alcohol, trifluridine, idoxuridine, cidofovir, gancyclovir, podofilox, podophyllotoxin, ribavirin, abacavir, delavirdine, didanosine, cfavirenz, lamivudine, nevirapine, stavudine, zalcitabine, zidovudine, amprenavir, indinavir, nelfinavir, ritonavir, saquinavir, amantadine, interferon, oseltamivir, ribavirin, rimantadine, zanamivir, or combinations thereof. Examples of antibacterial drugs include, but are not limited to, crythromycin, clindamycin, tetracycline, bacitracin, neomycin, mupirocin, polymyxin B, quinolones such as ciproflaxin, or combinations thereof. The therapeutic agents can also include immune modulating agents, including, but not limited to, imiquimod. Examples of therapeutic agents for treating photo damaged skin include, but are not limited to, immune modulating agents or immune activators which are capable of increasing immunity of the human skin mucosa. Non-limiting examples of such drugs include imiquimod, rosiquimod, or combinations thereof. When the dermatological condition is alopecia, the therapeutic agent can include, but is not limited to, corticosteroids, such as betamethasone dipropionate, halobetasol propionate, diflorasone diacetate, triamcinolone acetonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, hydrocortisone acetate, minoxidil, spironolactone, finasteride, anthralin, tretinoin topical immunotherapeutic agents such as dinitrochlorobenzene, squaric acid dibutyl ester, diphenylcyclopropenone, other hair growth stimulants, or combinations thereof. When the dermatological condition is psoriasis or dermatitis, the therapeutic agent can include, but is not limited to, corticosteroids, immune modulators, vitamin D3, retinoic acids, or combinations thereof; specific non-limiting examples of such drugs include betamethasone dipropionate, clobetasol propionate, halobetasol propionate, diflorasone diacetate, amcinonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, hydrocortisone acetate, tacrolimus, picrolimus, tazarotene, isotretinoin, cyclosporin, anthralin, vitamin D3, cholecalciferol, calcitriol, calcipotriol, tacalcitol, calcipotriene, or combinations thereof.

In another embodiment, the substance of interest comprises a cosmetic/cosmecuetical agent. The cosmetic/cosmeceutical agent may be selected from small molecules and large biotechnology produced or purified molecules (e.g., peptides, proteins, DNA, RNA). Examples of biologically active and biologically inactive cosmetic/cosmeceutical agents, which may include their analogues and antagonists, include, but are not limited to, antiaging products (exfoliants, keratolytic agents, anticellulite agents, antiwrinkle agents, and the like); skin protectants (sunscreens, barrier creams, oils, silicones, insect repellants, itch relief, antiseptics, disinfectants, skin tightening and toning milks and lotions, wart removal compositions, and the like); skin color products (whiteners, lighteners, sunless tanning accelerators, and the like); pigmented skin colorants (face and body makeups, foundation creams, mascara, rouge, lip products, and the like); bath and shower products (body cleansers, body wash, shower gel, liquid soap, soap bars, conditioning liquid bath oil, bath powders, and the like); foot care products, such as keratolytic corn and callous removers, foot soaks, and foot powders (medicated, such as antifungal athlete's foot powder, ointments, sprays, and the like); and antiperspirant powders.

Compositions

Compositions that include microneedle particles are also provided. In embodiments, the compositions include (i) a plurality of microneedle particles, and (ii) a liquid medium in which the plurality of microneedle particles is dispersed. The plurality of microneedle particles may be at least substantially evenly dispersed in the liquid medium, or unevenly dispersed in the liquid medium. The composition may be adapted for application to a biological tissue surface, such as mammalian skin.

Essentially any biocompatible liquid medium may be used. In some embodiments, the liquid medium may be a viscous liquid, a gel, or an emulsion. The liquid may have a viscosity of at least 1,000 cP. In embodiments, the liquid has a viscosity of about 1,000 cP to about 200,000 cP, about 1,000 cP to about 150,000 cP, about 1,000 cP to about 100,000 cP, about 1,000 cP to about 75,000 cP, or about 1,000 cP to about 50,000 cP. In some other embodiments, the liquid medium may be a non-viscous liquid, which is a liquid having a viscosity less than 1,000 cP, for example, about 5 cP to about 500 cP, about 5 cP to about 250 cP, or about 5 cP to about 100 cP. The liquid medium may be an aqueous medium and/or a non-aqueous medium. In one embodiment, the liquid medium comprises a bioactive agent and/or other substance of interest. Non-limiting examples of bioactive agents that may be included in the composition include drugs, sensors, cosmeceuticals, or a combination thereof.

The liquid medium of the composition may further include stabilizers, pH modifiers, thickening agents, or other pharmaceutically acceptable excipients, such as those known in the art for use in topical therapeutic applications, including materials that listed as Generally Recognized as Safe (GRAS) by the U.S. Food and Drug Administration.

Methods of Delivering a Substance of Interest and Treating Skin

Methods are provided for delivering a substance of interest and/or for treating skin using the microneedle particles described herein. Compositions and kits for carrying out such methods are also provided.

In embodiments, the methods of treating skin include contacting a region of skin with a plurality of microneedle particles, wherein the plurality of microneedle particles comprises microneedle particles having a core structure and one or more microneedles extending from the core structure, the one or more microneedles having a structure capable of at least partially penetrating skin.

Not wishing to be bound by any particular theory, it is believed that the electrical resistance of the region of skin may be reduced when at least a portion of the plurality of microneedle particles at least partially penetrates the region of skin.

In one embodiment, the contacting of the region of skin with the microneedle particles is effective to facilitate collagen generation of the region of skin. That is, the formation of microchannels in the region of skin contacted by the microneedle particles may induce a detectable increase or initiation of collagen generation, without the addition of any bioactive agent, or in combination with a bioactive agent.

In embodiments, the method of delivering a substance of interest includes contacting an area of skin or another biological tissue surface with a plurality of the microneedle particles provided herein in a manner effective to form a plurality of microchannels in the biological tissue surface, which yields a pre-treated biological tissue area; and applying a substance of interest to the pre-treated biological tissue area. Not wishing to be bound by any particular theory, it is believed that the methods of delivering a substance of interest may permit a substance of interest, such as a bioactive agent, to be delivered into the biological tissue so that the substance of interest may have a biological effect on the tissue. When the tissue is skin, the substance of interest may treat dermatological indications, impart cosmetic improvements to the skin, change the appearance of the skin, or a combination thereof.

As used herein, the phrase "at least partially penetrate a biological tissue" or the terms "penetrate" or "penetration" refer to the insertion of at least 25% of a microneedle of a microneedle particle, including at least the tip of the microneedle, into a biological tissue. In a preferred embodiment, the "penetration" includes piercing the stratum corneum of the skin of a human patient such that at least the tip end portion of the microneedle is within or has passed across the viable epidermis.

In embodiments, contacting a biological tissue surface or a region of skin with the plurality of the microneedle particles comprises applying one or more forces to the microneedle particles to ensure that at least a portion of the one or more microneedles at least partially penetrates the skin or other biological tissue at the intended site of application. The one or more forces may include a transverse force (e.g., perpendicular to the tissue surface), a shearing force (e.g., parallel to the tissue surface), or a combination thereof. For example, a gentle rubbing motion may be applied to the microneedle particles. As a further example, the biological tissue or region of skin may be contacted with a gas stream comprising the plurality of microneedle particles, wherein the gas stream imparts energy to the microneedle particles that is sufficient to permit at least a portion of the microneedles to at least partially penetrate the biological tissue or region of skin.

At least a portion of the microneedle particles may be combined with one or more other materials prior to, during, or after the plurality of microneedle particles contact the biological tissue or region of skin. As detailed above, in some embodiments, the plurality of microneedle particles is dispersed in a liquid medium, or the plurality of microneedle particles and the substance of interest are dispersed together in a liquid medium. The liquid medium may include a viscous liquid, a gel, or an emulsion. The liquid may have a viscosity of at least 500 cp, at least 600 cp, at least 700 cp, at least 800 cp, at least 900 cp, or at least 1,000 cp. The liquid medium may be an aqueous medium and/or a non-aqueous medium.

The contacting of the biological tissue surface with the plurality of microneedle particles and the applying of the substance of interest may occur simultaneously or separately. In embodiments, the contacting of the biological tissue surface with the plurality of microneedle particles and the applying of the substance of interest occur simultaneously. In some embodiments, the plurality of microneedle particles and the substance of interest are dispersed together in a liquid medium, and the contacting of the biological tissue surface with the plurality of microneedle particles and the applying of the substance of interest occur simultaneously. For example, the plurality of microneedle particles and the substance of interest may be dispersed in a liquid medium, and the contact of the biological tissue with the plurality of the microneedle particles may comprise applying and/or rubbing the liquid medium on the biological tissue surface.

The biological tissue generally may include any tissue that may be at least partially penetrated by the one or more microneedles of the microneedle particles. Non-limiting examples of biological tissues having surfaces that may be contacted with the plurality of microneedle particles include skin, eye (e.g., cornea, conjunctiva), gastrointestinal tract (e.g., mouth, esophagus, stomach, small and large intestine, rectµm, and anus), inside of nose, vagina, inside of car (e.g., car drum), muscle, blood vessels, cellular membranes, or a combination thereof. The biological tissues may be mammalian biological tissues, such as mammalian skin.

Generally, any amount or concentration of microneedle particles may be applied to a biological tissue, including amounts or concentrations at least sufficient to permit the passage of a desired amount of a substance of interest (e.g., a bioactive agent) into or through the biological tissue. In embodiments, the plurality of microneedle particles includes an amount of microneedle particles sufficient to achieve a concentration of about 5 to about 3,000 microneedle particles per cm$^2$ of the biological tissue surface area; about 10 to about 2,500 microneedle particles per cm$^2$ of the biological tissue surface area; about 10 to about 2,000 microneedle particles per cm$^2$ of the biological tissue surface area; about 20 to about 2,000 microneedle particles per cm$^2$ of the biological tissue surface area; about 50 to about 2,000 microneedle particles per cm$^2$ of the biological tissue surface area; about 50 to about 1,500 microneedle particles per cm$^2$ of the biological tissue surface area; about 50 to about 1,000 microneedle particles per cm$^2$ of the biological tissue surface area; about 100 to about 1,000 microneedle particles per cm$^2$ of the biological tissue surface area; about 100 microneedle particles per cm$^2$ of the biological tissue surface area; about 250 microneedle particles per cm$^2$ of the biological tissue surface area; about 500 microneedle particles per cm$^2$ of the biological tissue surface area; or about 1,000 microneedle particles per cm$^2$ of the biological tissue surface area. In other embodiments, in the compositions provided herein, the plurality of microneedle particles includes an amount of microneedle particles sufficient to achieve a concentration of microneedle particles in the liquid medium of about 10 to about 10,000 particles per cm$^3$ of the liquid medium, about 10 to about 5,000 particles per cm$^3$ of the liquid medium, about 10 to about 4,000 particles per cm$^3$ of the liquid medium, about 10 to about 3,000 particles per cm$^3$ of the liquid medium, about 10 to about 2,000 particles per cm$^3$ of the liquid medium, about 10 to about 1,500 particles per cm$^3$ of the liquid medium, about 20 to about 1,500 particles per cm$^3$ of the liquid medium, about 50 to about 1,000 particles per cm$^3$ of the liquid medium, or about 100 to about 1,000 particles per cm$^3$ of the liquid medium.

In embodiments, the methods provided herein include forming a plurality of microchannels in the biological tissue surface (i.e., micronchannels that originate at the outer surface of the biological tissue and penetrate deeper into the biological tissue below the outer surface). The microchannels generally form when the one or more microneedles at least partially penetrate a biological tissue. The microchannels may permit passage of a substance of interest into the biological tissue before and/or after removal of a microneedle particle from the biological tissue surface. The removal of the microneedle particles from a biological tissue may be achieved by any means, including rinsing, wiping, applying and removing an adhesive material, or any combination thereof. The microchannels may be at least substantially symmetrical in cross-sectional arca.

In embodiments, the microneedle particles may be applied with an applicator. An "applicator" is any device that stores and/or assists with the contacting of a biological tissue with the microneedle particles. In one embodiment, the applicator comprises a reservoir containing the microneedle particles and a roller or other apparatus that permits the contacting of a biological tissue with the microneedle particles. In another embodiment, the applicator is a rigid or deformable container that is open on at least one side that is placed in contact with the biological tissue and is closed on at least one side that is not in contact with the biological tissue. In yet another embodiment, the applicator comprises an apparatus that creates a gas stream capable of delivering the microneedle particles to a biological tissue. In a further embodiment, the applicator comprises a solid, gel, viscous liquid, or other formulation comprising a plurality of microneedle particles. This solid formulation may contact a biological tissue to transfer the microneedle particles to the biological tissue. As part of these and other embodiments, there may be a handle or other feature of the applicator that facilitates grabbing, holding, moving or otherwise operating the applicator with fingers and/or hand to apply microneedle particles to the biological tissue. The applicator may be manually operated or may include one or more moveable components of the applicator that are otherwise powered, for example, electrically, such as by a battery. The moveable components may facilitate movement of the microneedle particles toward, away from, along, and/or into the surface of the biological tissue. The applicator may be part or all of the packaging or housing that stores the microneedle particle formulation. In one embodiment, a microneedle particle formulation is dispensed (e.g., squeezed) from its packaging onto a biological tissue surface, and then all or a part of the packaging is used as an applicator.

In one embodiment, the applicator is in the form a wipe. The wipe may include a base layer and a release layer which includes the microneedle particles. The release layer may include a gel, paste, or other semi-solid carrier medium in which the microneedle particles are dispersed. The base layer may include a polymeric film or a woven or non-woven fabric suitable for temporarily carrying the release layer until the release layer can be wiped onto a biological tissue surface, for example onto a wet or dry skin surface.

As used in this specification and the appended claims, the singular forms "a," "an," and "the" include plural referents unless the content clearly dictates otherwise. Thus, for example, reference to "a barrier material" can include a combination of two or more components; reference to "a predefined fracture region" can include two different predefined fracture regions, and the like. The term "about", as used herein, indicates the value of a given quantity can include quantities ranging within 10% of the stated value, or optionally within 5% of the value, or in some embodiments within 1% of the value.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Production of Microneedle Particles

A plurality of microneedle particles having four planar microneedles was produced from a sheet of stainless steel having a thickness of about 12 μm. A double-sided adhesive tape was applied to the sheet of stainless steel, and then infrared laser ablation (Q-switched Nd: YLF, 1047 nm) was used to cut the microneedles particles having four planar microneedles from the sheet of stainless steel.

The microneedle particles were removed from the stainless steel sheet by peeling the adhesive off of the stainless steel sheet. The microneedle particles were then placed in a solvent to dissolve the adhesive.

Two batches of microneedle particles were made using this method. In the first batch, the greatest dimension of the microneedle particles was 800 μm, and, in the second batch, the greatest dimension of the microneedle particles was 350 μm.

Example 2—Gentian Violet Staining of Microchannels

An in vitro sample of porcine ear skin was stained with gentian violet stain after the ear skin was pre-treated ex vivo with aloe vera gel (negative control), a microneedle patch (positive control), the microneedle particles of Example 1 at a concentration of 1000 particles/cm$^2$ of car skin (4-1000), and the microneedle particles of Example 1 at a concentration of 500 particles/cm$^2$ of car skin (4-500). The microneedle particles of Example 1, in both instances, were applied by disposing the microneedle particles in aloe vera gel, and gently rubbing the aloe vera gel on the car skin. The microneedle patch (positive control) was a 10×10 microneedle array (about 700 μm in length).

Figure 9:
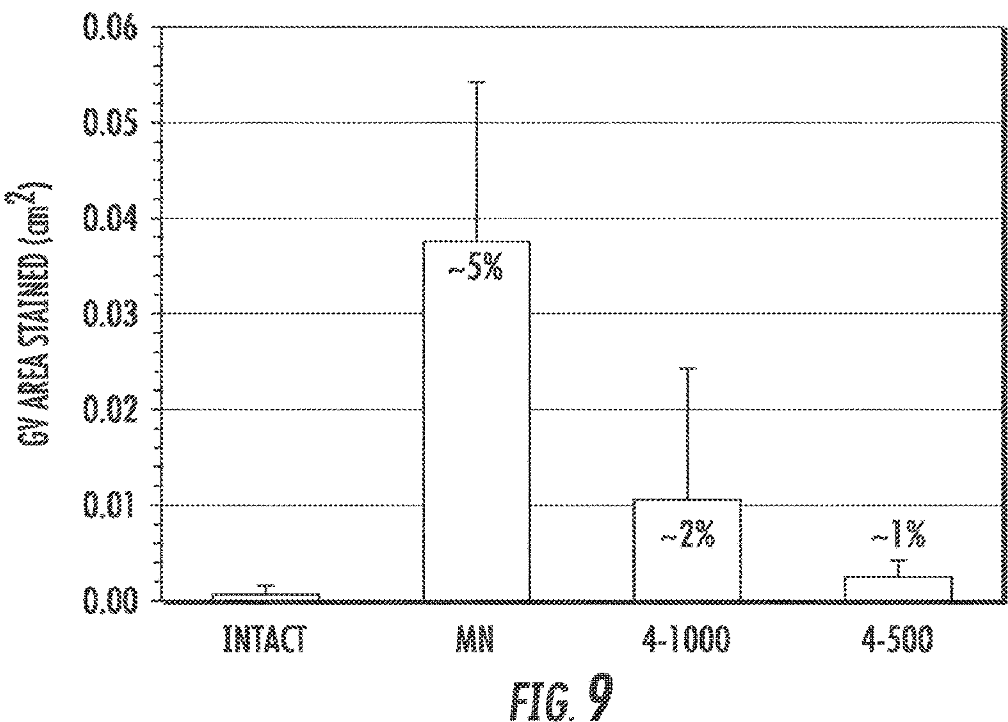
FIG. 9 depicts the area ($cm^2$) of porcine skin samples stained by gentian violet stain after pre-treatment with a microneedle patch and two embodiments of microneedle particles.

Representative processed images (ImageJ) were then used to determine the total area and number of penetration sites based on gentian violet staining. The increase in stained area observed with the microneedle patch and the two microneedle particles pre-treatments is depicted at FIG. 9.

Figure 10:
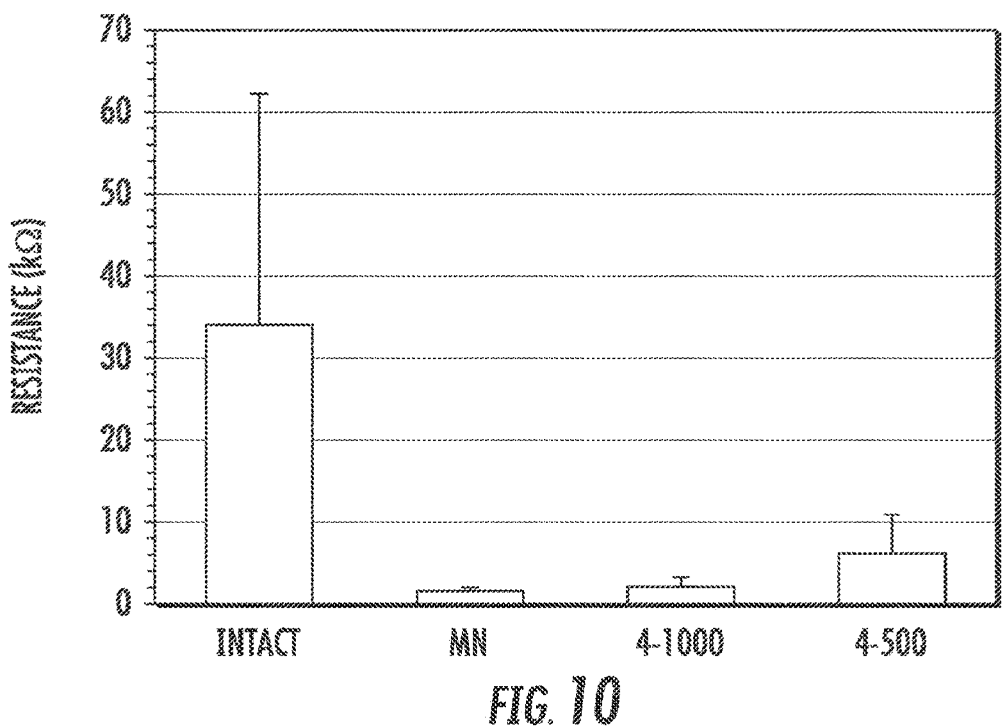
FIG. 10 depicts the electrical resistance of porcine skin samples after pre-treatment with a microneedle patch and two embodiments of microneedle particles.

After the gentian violet dye was applied, each car skin sample was incubated in phosphate-buffered saline (PBS) overnight. The electrical resistance of each ear skin sample was then measured (FIG. 10). The skin electrical resistance decreased after pre-treatment with the microneedle patch and the two types of microneedle particles.

Not wishing to be bound by any particular theory, it was believed that the measurements of gentian violet staining area and skin electrical resistance provided insight into the reduction of skin barrier properties due to pre-treatment with embodiments of microneedle particles.

Example 3—Treatment of Porcine Ear Skin with Sulforhodamine B

As in Example 1, an in vitro sample of porcine car skin was pre-treated ex vivo with aloe vera gel (negative control), a microneedle patch (positive control), the microneedle particles of Example 1 at a concentration of 1000 particles/cm$^2$ of car skin (4-1000), and the microneedle particles of Example 1 at a concentration of 500 particles/cm$^2$ of car skin (4-500). After the pre-treatment, each ear skin sample was subjected to 10 μM sulforhodamine B in a vertical Franz diffusion cell setup.

Figure 11:
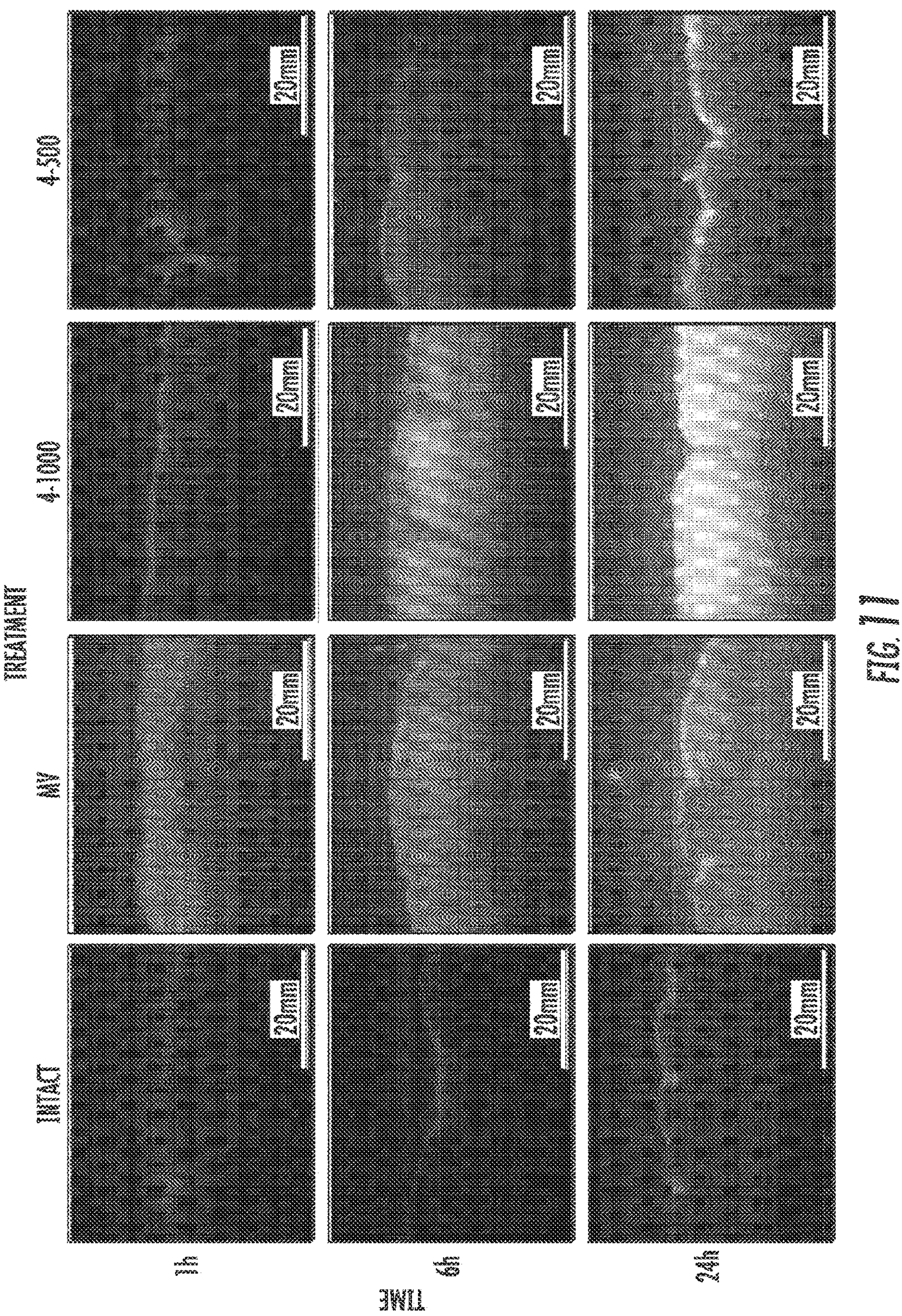
FIG. 11 includes histological cross sections of skin samples pre-treated with a microneedle patch or one of two embodiments of microneedle particles at 1 hour, 6 hours, and 24 hours after application of the sulforhodamine B.

At 1 hour, 6 hours, and 24 hours after application of the sulforhodamine B, fluorescence images of histological cross sections of each car skin sample were analyzed, as depicted at FIG. 11.

Example 4—Effect of Microneedle Particle Concentration

In the following examples, the microneedle particles' properties were characterized in relation to their effects on increasing the permeability of cutaneous tissue to topically applied compounds.

The effect of microneedle particle concentration was tested by applying microneedle particles to porcine car skin at concentrations of 100 microneedle particles/cm$^2$, 500 microneedle particles/cm$^2$, 1,000 microneedle particles/cm$^2$, and 2,000 microneedle particles/cm$^2$. In this example, three types of microneedle particles, each having a different geometry, were tested. The first, second, and third type of microneedle particles had two microneedles, four microneedles, and six microneedles, respectively.

Figure 12:
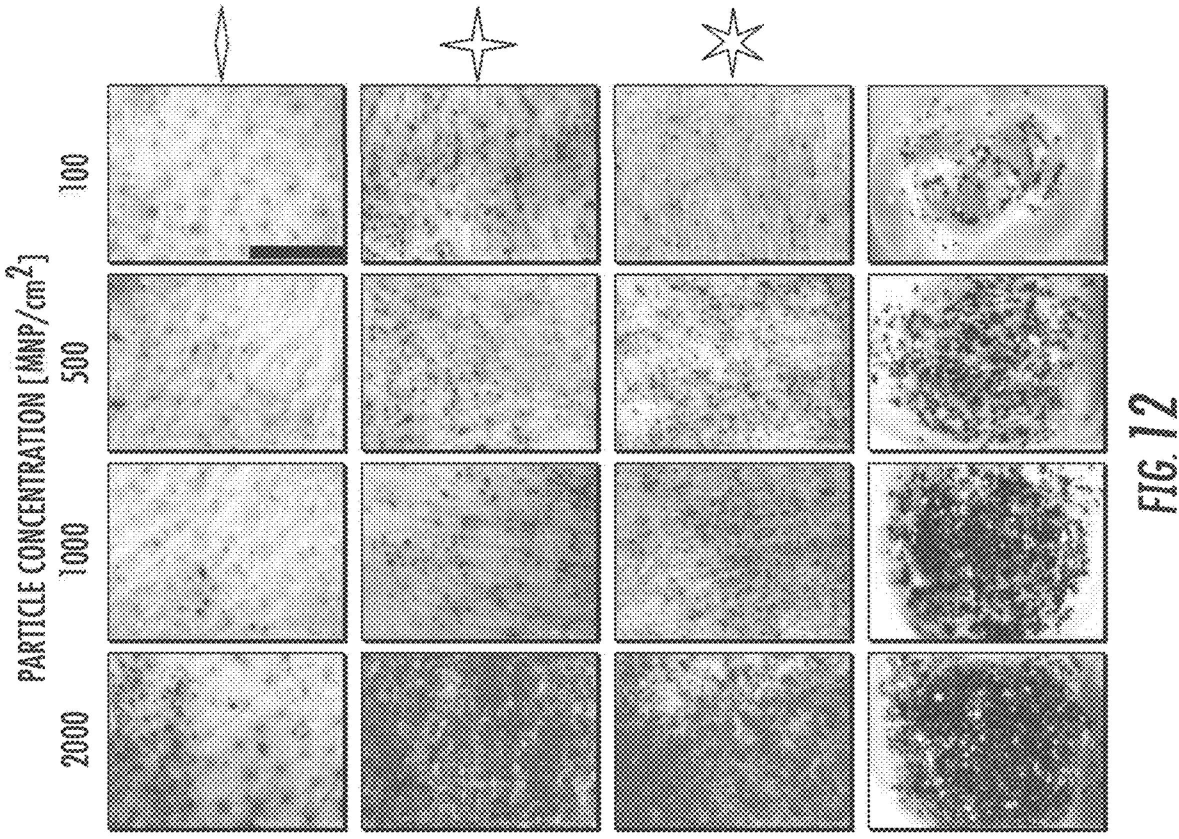
FIG. 12 depicts the penetration sites achieved by three embodiments of microneedle particles at four different concentrations (scale bar=5 mm); also depicted are microneedle particles in a gel formulation at four different microneedle concentrations.

The samples of porcine car skin were pre-treated with the microneedle particles of this example by applying the microneedle particles onto the car skin for about 10 seconds. The microneedle particles were combined with aloe vera gel prior to pre-treating the skin samples of this example. The car skin was subsequently stained with gentian violet, and the penetration sites are shown at FIG. 12. FIG. 12 generally shows that the increase in the concentration of microneedle particles caused an increase in the number of penetration sites. In FIG. 12, the column farthest to the right visually depicts the concentration of the microneedle particles in the aloe vera gel applied to the skin samples.

Example 5—Effect of Microneedle Particle Geometry

The effect of microneedle particle geometry was tested by applying three types of microneedle particles having different geometries to samples of porcine ear skin at the same concentrations. The first type of microneedle particles had two microneedles, the second type of microneedle particles had four microneedles, the third type of microneedle particles had six microneedles, and three sizes of each type of microneedle particles were tested: 500 μm, 1,000 μm, and 2,000 μm (these distances refer to the "greatest dimension of the microneedle particles"). The microneedle particles of this example were referred to as follows in the relevant figures:

| Size of Microneedle Particles (μm) | 2 Planar Microneedles | 4 Planar Microneedles | 6 Planar Microneedles |
|---|---|---|---|
| 500 | 2-500 | 4-500 | 6-500 |
| 1,000 | 2-1000 | 4-1000 | 6-1000 |
| 2,000 | 2-2000 | 4-2000 | 6-2000 |

The samples of porcine ear skin were pre-treated with the microneedles of this example by applying the microneedle particles in aloe vera gel on the car skin for about 10 seconds. The car skin was subsequently stained with gentian violet, and an analysis of the penetration sites revealed that, at least in this example, a decrease in the size of the microneedle particles resulted in a decrease in the number of penetration sites.

Figure 13A:
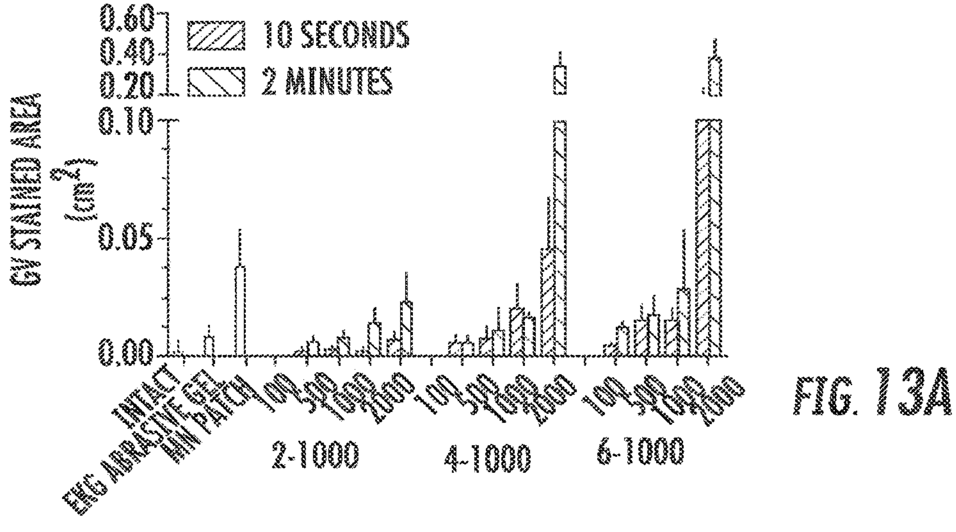
FIG. 13A depicts graphically how the gentian violet stained area was affected by altering the length of time several embodiments of microneedle particles were applied to skin, the concentration of the microneedle particles, and the number of microneedles per microneedle particle.
Figure 13B:
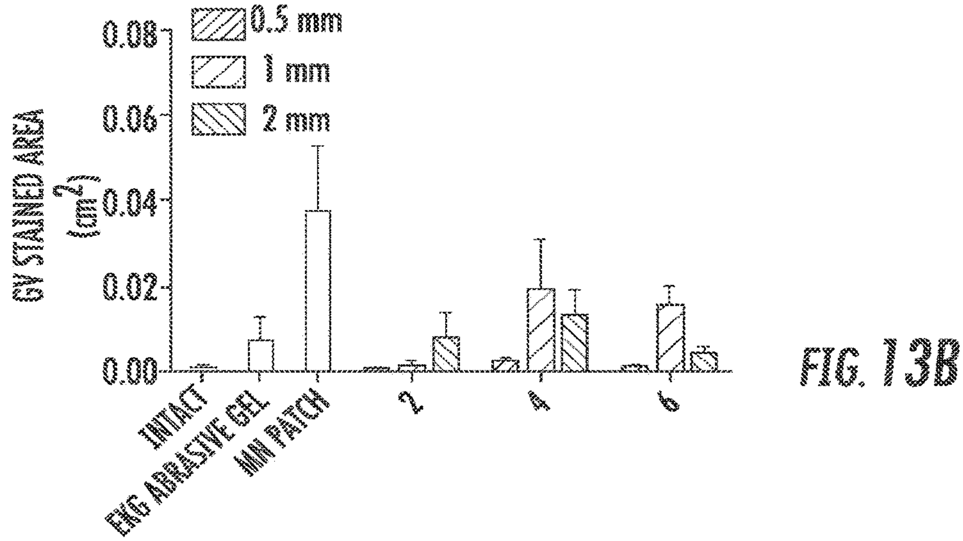
FIG. 13B depicts graphically how the gentian violet stained area was affected by altering the size of several embodiments of microneedle particles, and the number of microneedles per microneedle particle.
Figure 13C:
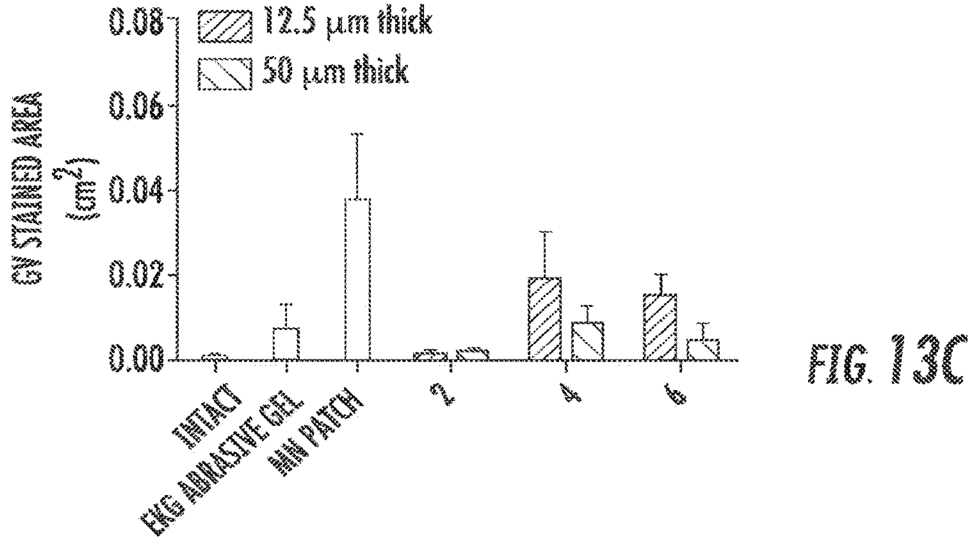
FIG. 13C depicts graphically how the gentian violet stained area was affected by altering the thickness of several embodiments of microneedle particles, and the number of microneedles per microneedle particle.
Figure 14A:
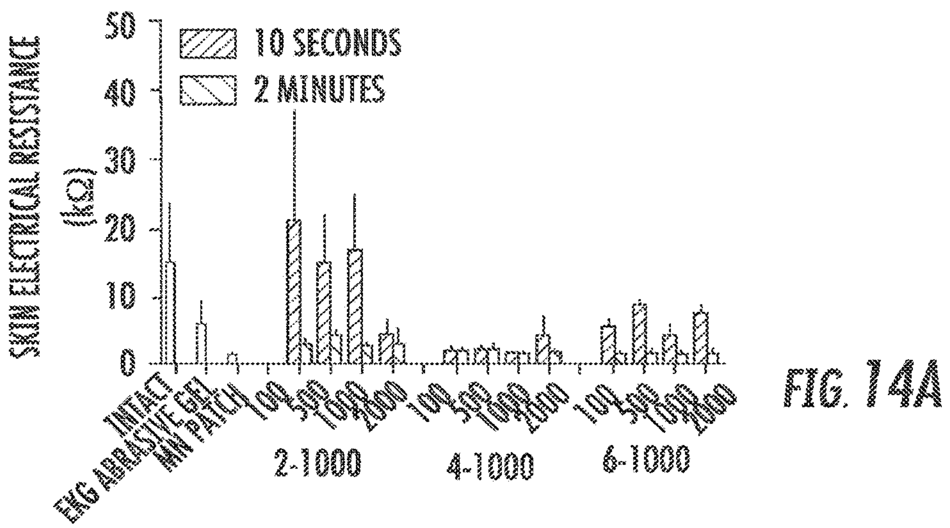
FIG. 14A depicts graphically how the skin electrical resistance was affected by altering the length of time several embodiments of microneedle particles were applied to skin, the concentration of the microneedle particles, and the number of microneedles per microneedle particle.
Figure 14B:
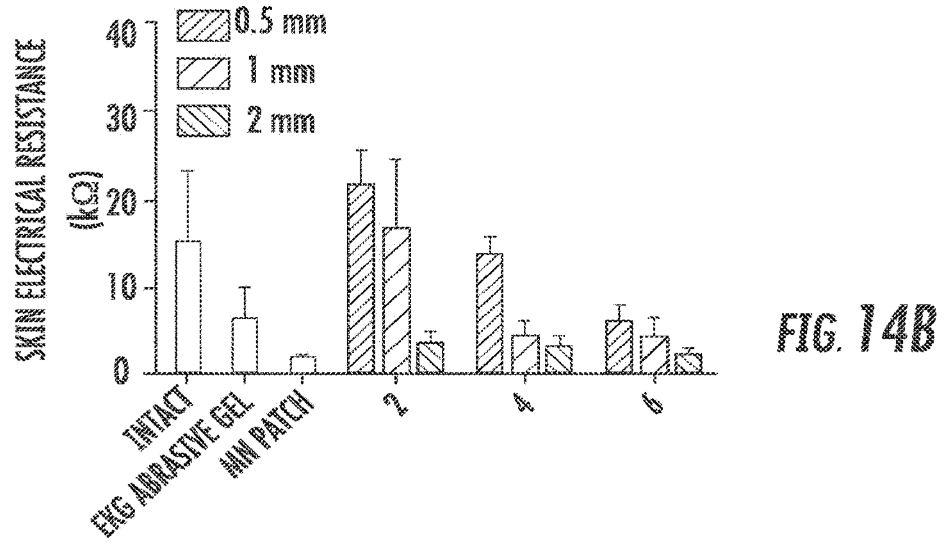
FIG. 14B depicts graphically how the skin electrical resistance was affected by altering the size of several embodiments of microneedle particles, and the number of microneedles per microneedle particle.
Figure 14C:
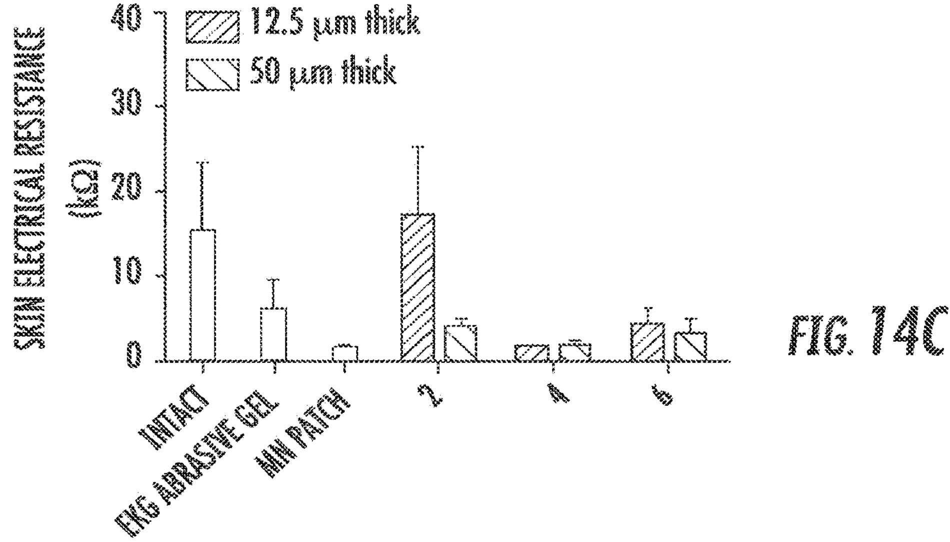
FIG. 14C depicts graphically how the skin electrical resistance was affected by altering the thickness of several embodiments of microneedle particles, and the number of microneedles per microneedle particle.
Figure 15A:
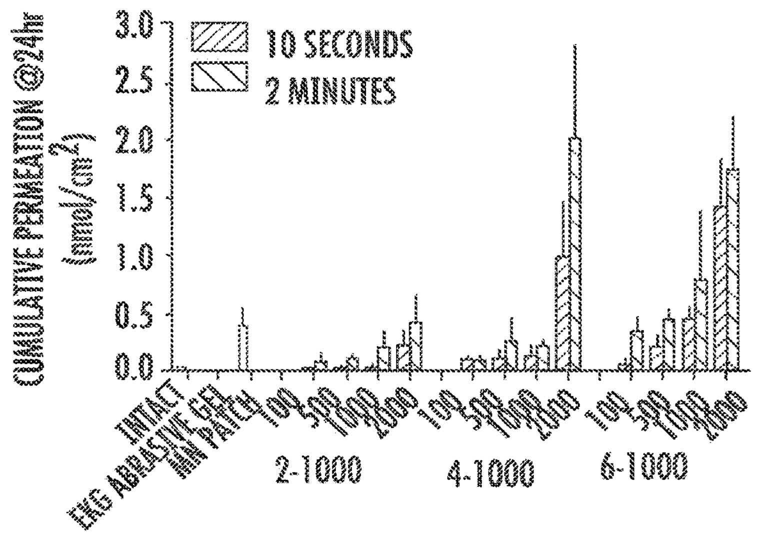
FIG. 15A depicts graphically how the cumulative permeation of sulforhodamine B across the skin at 24 hours was affected by altering the length of time several embodiments of microneedle particles were applied to skin, the concentration of the microneedle particles, and the number of microneedles per microneedle particle.
Figure 15B:
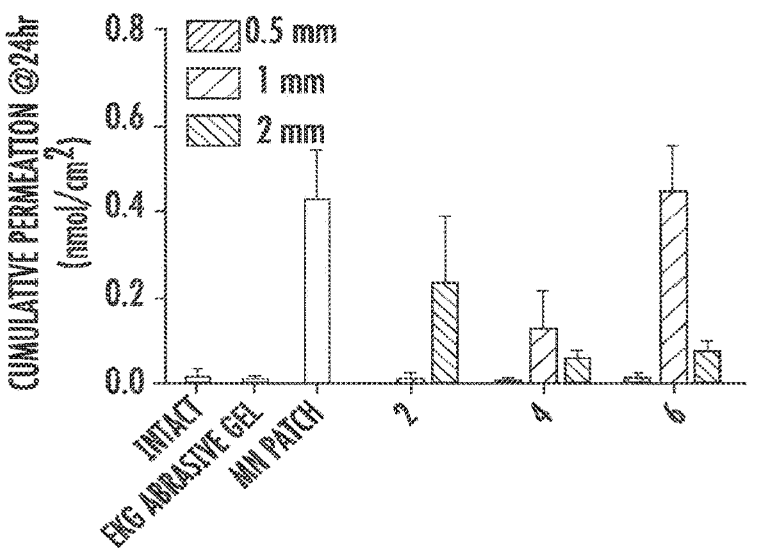
FIG. 15B depicts graphically how the cumulative permeation of sulforhodamine B across the skin at 24 hours was affected by altering the size of several embodiments of microneedle particles, and the number of microneedles per microneedle particle.
Figure 15C:
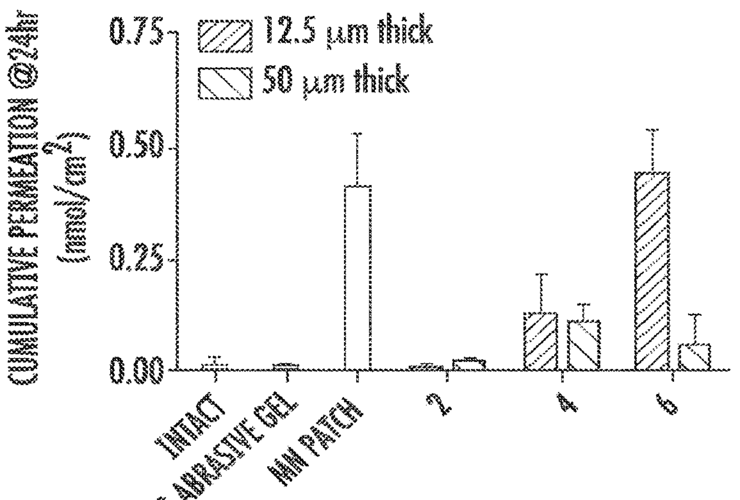
FIG. 15C depicts graphically how the cumulative permeation of sulforhodamine B across the skin at 24 hours was affected by altering the thickness of several embodiments of microneedle particles, and the number of microneedles per microneedle particle.
Figure 16A:
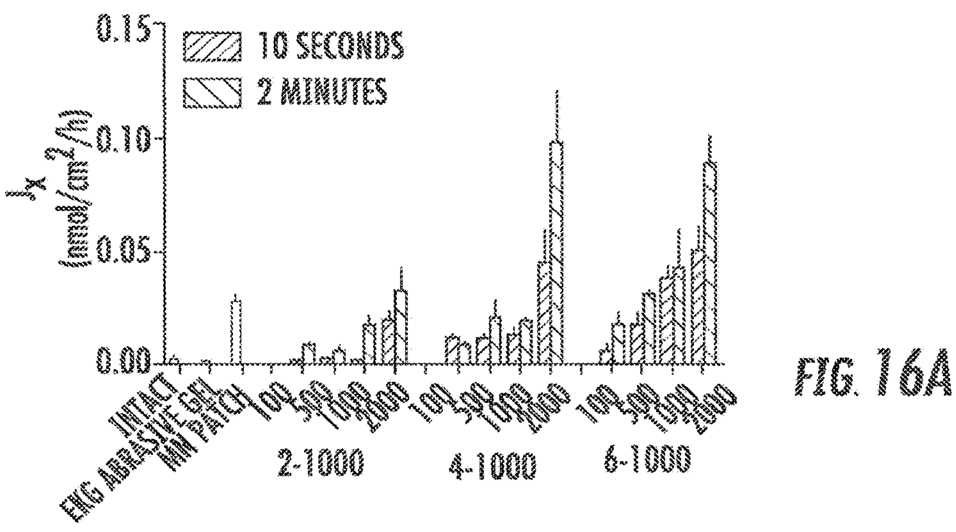
FIG. 16A depicts graphically how transdermal flux of sulforhodamine B across the skin, $J_x$, was affected by altering the length of time several embodiments of microneedle particles were applied to skin, the concentration of the microneedle particles, and the number of microneedles per microneedle particle.
Figure 16B:
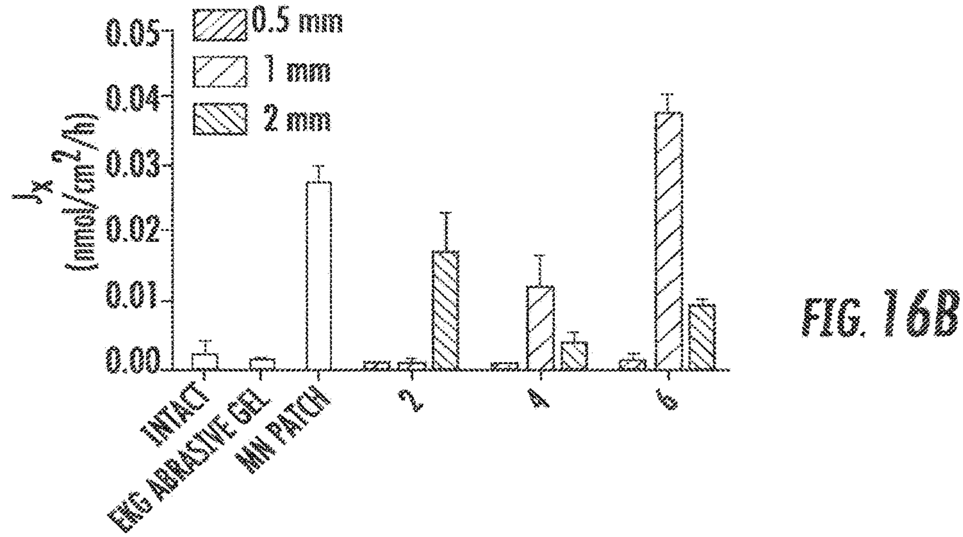
FIG. 16B depicts graphically how transdermal flux of sulforhodamine B across the skin, $J_x$, was affected by altering the size of several embodiments of microneedle particles, and the number of microneedles per microneedle particle.
Figure 16C:
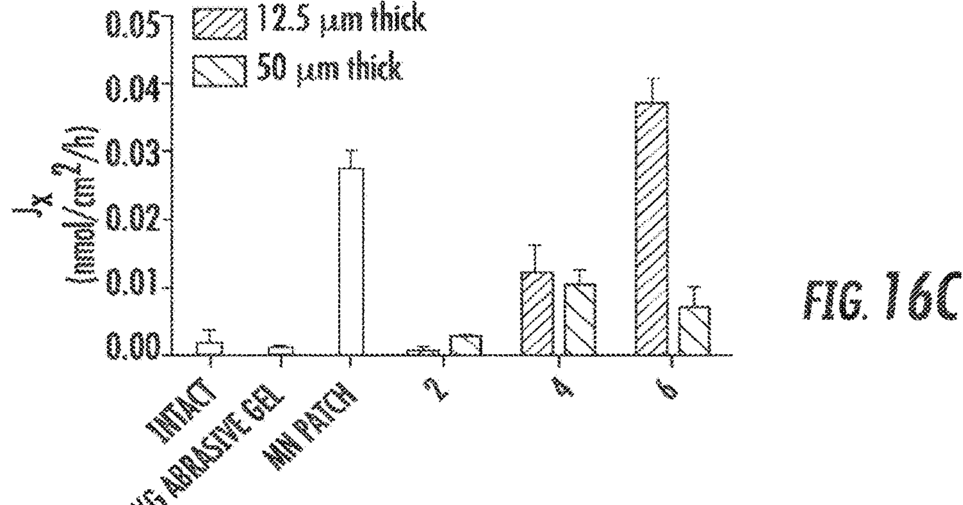
FIG. 16C depicts graphically how transdermal flux of sulforhodamine B across the skin, $J_x$, was affected by altering the thickness of several embodiments of microneedle particles, and the number of microneedles per microneedle particle.

FIG. 13A, FIG. 13B, and FIG. 13C depict how the gentian violet stained area was affected by altering the length of time the microneedle particles were applied to the car skin, the concentration of the microneedle particles, and the number of microneedles per microneedle particle (FIG. 13A); the size of the microneedle particles, and the number of microneedles per microneedle particle (FIG. 13B), and the thickness of the particles, and the number of microneedles per microneedle particle (FIG. 13C). FIG. 14A, FIG. 14B, and FIG. 14C depict how the skin electrical resistance, as measured according to the procedure provided at Example 2, was affected by altering the length of time the microneedle particles were applied to the car skin, the concentration of the microneedle particles, and the number of microneedles per microneedle particle (FIG. 14A); the size of the microneedle particles, and the number of microneedles per microneedle particle (FIG. 14B), and the thickness of the particles, and the number of microneedles per microneedle particle (FIG. 14C). FIG. 15A, FIG. 15B, and FIG. 15C depict how the cumulative permeation at 24 hours (nmol/cm$^2$) of sulforhodamine B across the skin was affected by altering the length of time the microneedle particles were applied to the car skin, the concentration of the microneedle particles, and the number of microneedles per microneedle particle (FIG. 15A); the size of the microneedle particles, and the number of microneedles per microneedle particle (FIG. 15B), and the thickness of the particles, and the number of microneedles per microneedle particle (FIG. 15C). FIG. 16A, FIG. 16B, and FIG. 16C depict how the transdermal flux of sulforhodamine B, Jx (nmol/cm$^2$/h), was affected by altering the length of time the microneedle particles were applied to the car skin, the concentration of the microneedle particles, and the number of microneedles per microneedle particle (FIG. 16A); the size of the microneedle particles, and the number of microneedles per microneedle particle (FIG. 16B), and the thickness of the particles, and the number of microneedles per microneedle particle (FIG. 16C).

A test also was conducted to determine the effect of particle size, geometry, and concentration on the cumulative permeation of the skin samples. Samples of the 2-1000, 4-1000, and 6-1000 microneedle particles were each applied by rubbing an car skin sample for 10seconds and 2 minutes, and, for each time period, microneedle particle concentrations of 100, 500, and 1000 particles/cm$^2$ were tested. The test revealed that the time of application impacted the skin samples treated with 2-1000 particles more than those treated with the 4-1000 and 6-1000 particles. Specifically, the cumulative permeation (mmol/cm$^2$) at 48 hours of the skin samples treated with the 2-1000 particles for 2 minutes was significantly higher than the cumulative permeation at 48 hours of the skin sample treated with the 2-1000 particle for 10 seconds. In contrast, the time of application had less impact on the cumulative permeation at 48 hours of the skin samples treated with the 4-1000 and 6-1000 particles. For the skin samples treated with the 4-1000 and 6-1000 particles, increasing the concentration of the particles increased the cumulative permeation at 48 hours of the skin samples more than increasing the time of application.

Example 6—Delivery of Sulforhodamine B in vivo

Figure 17:
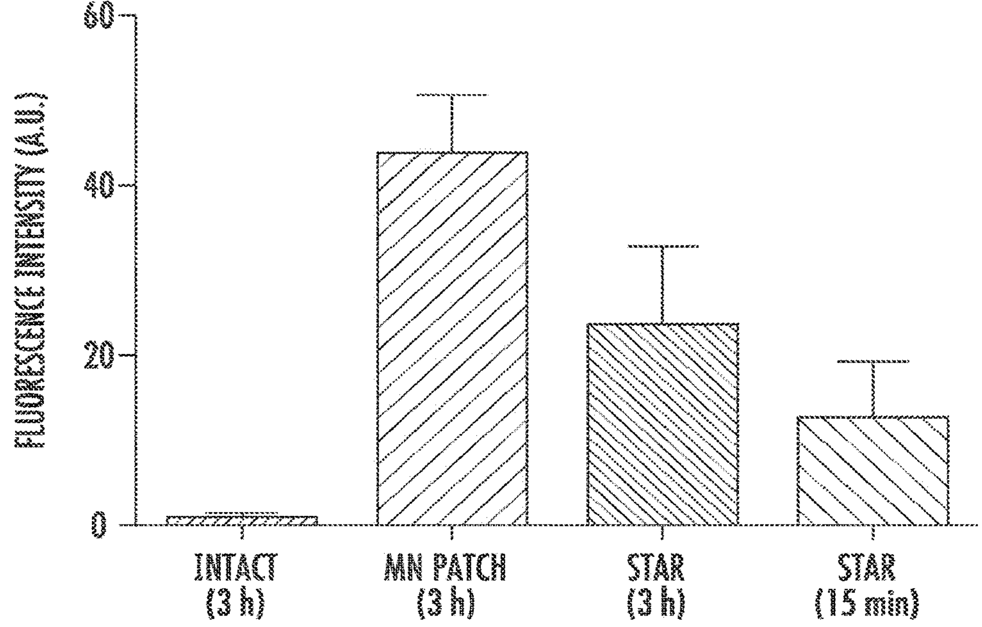
FIG. 17 depicts the fluorescence intensity of sulforhodamine B delivered into hairless rat skin in vivo treated with aloe vera gel, a microneedle patch, and an embodiment of microneedle particles.

Hairless rat skin samples in vivo were pre-treated with aloe vera gel, a microneedle patch, and the microneedle particles of Example 1. Sulforhodamine B solutions were placed on the skin for 3 hours for skin pre-treated with aloe vera gel or a microneedle patch, and was placed on the skin for either 3 hours or 15 minutes for the skin pre-treated with the microneedle particles of this example. The mean fluorescence intensity of sulforhodamine B delivered into the hairless rat skin was measured, as shown at FIG. 17.

Example 7—Production of Microneedle Particles

Ceramic microneedle particles having four planar microneedles were produced by laser etching microstructures into alumina green tape. A first portion of the microneedle particles were then used to treat a skin sample, and a second portion of the microneedle particles were sintered at about 1,500° C.

The sintering caused the microneedle particles of this example to shrink about 30%. It also was noticed that the sintered microneedle particles of this example had slightly sharper edges and tips than the pre-sintered microneedle particles of this example.

Example 8—Production of Microneedle Particles

Microneedle particles having four planar projections were produced in the example from poly-(lactic acid)(PLA). PLA microparticles were fabricated and Nile Red dye was encapsulated within the microparticles for visualization purposes. The Nile Red dye, therefore, was optional. The PLA microparticles were then cast into a polydimethylsiloxane (PDMS) mold having microneedle particle-shaped cavities. The PLA microparticles were melted into the PDMS molds. The PLA microneedle particles were allowed to cool and solidify, and then were demolded.

We claim:

1. A method of treating skin of a subject, the method comprising:

contacting a region of skin with a composition;

wherein the contacting is effective to form a plurality of microchannels in the stratum corneum of the region of skin;

wherein the composition comprises a plurality of microneedle particles, and a liquid medium in which the plurality of microneedle particles is dispersed;

wherein each of the microneedle particles comprises a core structure, and one or more microneedles extending from the core structure, the one or more microneedles being structured to penetrate the stratum corneum, and wherein at least one of (i) the core structure, (ii) the one or more microneedles, and (iii) a spatial relationship between/among two or more of the microneedles is configured to prevent the entire microneedle particle from penetrating the stratum corneum.

2. The method of claim 1, wherein the composition is dispersed onto the skin from an applicator.

3. The method of claim 2, wherein the applicator comprises a wipe.

4. The method of claim 1, further comprising contacting the region of skin with a substance of interest to produce a therapeutic effect in the subject or a cosmetic effect in the region of skin.

5. The method of claim 4, wherein the substance of interest comprises a bioactive agent.

6. The method of claim 4, wherein the substance of interest comprises a vaccine, an allergen, a vitamin, a cosmetic agent, a cosmeceutical, a diagnostic agent, or a marker.

7. The method of claim 4, wherein the liquid medium comprises a substance of interest, and wherein the substance of interest comprises a bioactive agent.

8. The method of claim 7, wherein the bioactive agent is selected from the group consisting of a protein, a peptide or fragment thereof, DNA, RNA, and a combination thereof.

9. The method of claim 1, wherein the contacting of the region of skin is effective to facilitate collagen generation of the region of skin.

10. The method of claim 1, wherein the region of skin is a region of mammalian skin.

11. The method of claim 1, wherein the liquid medium is a viscous liquid having a viscosity of at least 1,000 cP.

12. The method of claim 1, wherein the liquid medium is a gel.

13. The method of claim 1, wherein the liquid medium is a non-viscous liquid having a viscosity less than 1,000 cP.

14. The method of claim 1, wherein each of the microneedle particles comprises three microneedles, four microneedles, five microneedles, six microneedles, seven microneedles, eight microneedles, nine microneedles, or ten microneedles extending from the core structure.

15. The method of claim 1, wherein the one or more microneedles are substantially planar microneedles.

16. The method of claim 1, wherein each of the microneedle particles comprises three or more microneedles, and at least one of the three or more microneedles is a non-planar microneedle.

17. The method of claim 1, wherein each of the microneedle particles includes exactly four, five, or six microneedles, and at least one of the four, five, or six microneedles is a non-planar microneedle.

18. The method of claim 1, wherein each of the one or more microneedles independently has a length of about 10 μm to about 2,000 μm.

19. A method of treating skin of a subject, the method comprising:

contacting a region of skin with a composition, wherein the contacting is effective to form a plurality of microchannels in the stratum corneum of the region of skin; and contacting the region of skin with a substance of interest to produce a therapeutic effect in the subject or a cosmetic effect in the region of skin;

wherein the composition comprises a plurality of microneedle particles, and a liquid medium in which the plurality of microneedle particles is dispersed;

wherein each of the microneedle particles comprises a core structure, and one or more microneedles extending from the core structure, the one or more microneedles being structured to penetrate the stratum corneum, and wherein at least one of (i) the core structure, (ii) the one or more microneedles, and (iii) a spatial relationship between/among two or more of the microneedles is configured to prevent the entire microneedle particle from penetrating the stratum corneum surface; and wherein each of the one or more microneedles independently has a length of about 10 μm to about 2,000 μm.

20. The method of claim 19, wherein the substance of interest is a therapeutic agent effective in the treatment of a skin condition selected from alopecia, psoriasis, or dermatitis.

* * * * *